US012758554B2

(12) United States Patent
Barrett et al.

(10) Patent No.: US 12,758,554 B2
(45) Date of Patent: Oct. 13, 2026

(54) STABLE IMMEDIATE RELEASE TABLET AND CAPSULE FORMULATIONS OF 1-((2S,5R)-5-((7H-PYRROLO[2,3-D] PYRIMIDIN-4-YL)AMINO)-2-METHYLPIPERIDIN-1-YL)PROP-2-EN-1-ONE

(71) Applicant: Pfizer R&D UK Limited, Sandwich (GB)

(72) Inventors: Andrew Richard Barrett, Whitstable (GB); Ian Leonard Smales, Broadstairs (GB); Rand Dhiyaa Turki, Ramsgate (GB); Suet Mei Wong, London (GB)

(73) Assignee: Pfizer R&D UK Limited, Sandwich (GB)

( * ) Notice: Subject to any disclaimer, the term of this patent is extended or adjusted under 35 U.S.C. 154(b) by 1116 days.

(21) Appl. No.: 17/758,095

(22) PCT Filed: Dec. 29, 2020

(86) PCT No.: PCT/IB2020/062524

§ 371 (c)(1),
(2) Date: Jun. 28, 2022

(87) PCT Pub. No.: WO2021/137160

PCT Pub. Date: Jul. 8, 2021

(65) Prior Publication Data

US 2023/0338380 A1 Oct. 26, 2023

Related U.S. Application Data

(60) Provisional application No. 62/955,497, filed on Dec. 31, 2019.

(51) Int. Cl.

| | |
|---|---|
| ***A61K 31/519*** | (2006.01) |
| ***A61K 9/20*** | (2006.01) |
| ***A61K 9/48*** | (2006.01) |

(52) U.S. Cl.

CPC .......... *A61K 31/519* (2013.01); *A61K 9/2013* (2013.01); *A61K 9/2018* (2013.01); *A61K 9/2027* (2013.01); *A61K 9/2054* (2013.01); *A61K 9/4816* (2013.01); *A61K 9/4825* (2013.01); *A61K 9/4858* (2013.01); *A61K 9/4866* (2013.01)

(58) Field of Classification Search

None

See application file for complete search history.

(56) References Cited

U.S. PATENT DOCUMENTS 9,629,805 B2 * 4/2017 Karakatsani ......... A61K 31/222
10,034,882 B2 7/2018 Gupta et al.
2009/0060996 A1 * 3/2009 Kristjansson ............. A61P 7/02 514/301
2015/0110820 A1 * 4/2015 Laidler .................... C07K 7/08 424/185.1
2016/0022661 A1 * 1/2016 Stefan ..................... A61P 35/00 424/465

FOREIGN PATENT DOCUMENTS

EP 2481397 A1 * 8/2012 .......... A61K 9/2077
WO 2012100949 8/2012
WO 2015083028 6/2015
WO WO-2017064192 A1 * 4/2017 .......... A61K 31/197
WO 2020084435 4/2020

OTHER PUBLICATIONS

D'Amico et al. Expert Opinion on Investigational Drugs 2018 27(7): 595-599 (Year: 2018).*

PCT International application No. PCT/IB2020/062524, filed Dec. 29, 2020, International Preliminary Report on Patentability mailed Jul. 5, 2022 , 12 pages.

International Search Report and Written Opinion mailed Mar. 16, 2021 for International application No. PCT/IB2020/062524, filed Dec. 29, 2020, 19 pages.

Tao, Yong, et al., "Process Development and Scale Up of a Selective JAK3 Covalent Inhibitor PF-06651600", Organic Process Research & Development, Jul. 19, 2019, pp. 1872-1880, 23(9).

Thorarensen, Atli, et al., "Design of a Janus Kinase 3 (JAK3) Specific Inhibitor 1-((28,5R)-5-((7H-Pyrrolo[2,3d] pyrimidin-4-yl)amino)-2-methylpiperidin-1-yl)prop-2-en-1-one (PF-06651600) Allowing for the Interrogation of JAK3 Signaling in Humans", Journal of Medicinal Chemistry, Feb. 16, 2017, pp. 1971-1993, 60(5).

* cited by examiner

*Primary Examiner* — Robert A Wax
*Assistant Examiner* — Caralynne E Helm
(74) *Attorney, Agent, or Firm* — Zhigang Rao

(57) ABSTRACT

The present invention is directed to new stable immediate release tablet and capsule formulations for the Janus Kinase 3 (JAK3) inhibitor 1-((2S,5R)-5-((7H-pyrrolo[2,3-d]pyrimidin-4-yl)amino)-2-methylpiperidin-1-yl)prop-2-en-1-one para-toluenesulfonate having structure

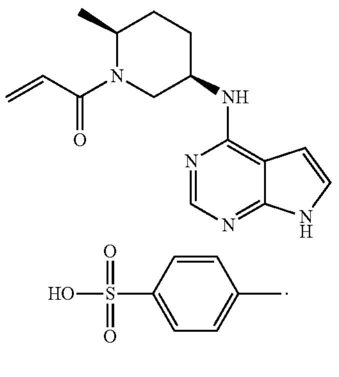

3 Claims, 29 Drawing Sheets

STABLE IMMEDIATE RELEASE TABLET AND CAPSULE FORMULATIONS OF 1-((2S,5R)-5-((7H-PYRROLO[2,3-D] PYRIMIDIN-4-YL)AMINO)-2-METHYLPIPERIDIN-1-YL)PROP-2-EN-1-ONE

This application is a national stage application under 35 U.S.C. 371 of PCT//IB2020/062524, filed on Dec. 29, 2020, which claims the benefit of U.S. Provisional Patent Application No. 62/955,497, filed on Dec. 31, 2019, the disclosures of which are hereby incorporated by reference in their entirety.

FIELD OF THE INVENTION

The present invention relates to the discovery of stable immediate release formulations for the Janus Kinase 3 (JAK3) inhibitor 1-((2S,5R)-5-((7H-pyrrolo[2,3-d]pyrimidin-4-yl)amino)-2-methylpiperidin-1-yl)prop-2-en-1-one as its para-toluenesulfonate salt (PF-06651600-15).

BACKGROUND OF THE INVENTION 1-((2S,5R)-5-((7H-Pyrrolo[2,3-d]pyrimidin-4-yl)amino)-2-methylpiperidin-1-yl)prop-2-en-1-one is a selective and irreversible Janus Kinase 3 (JAK3) inhibitor being investigated for the treatment of alopecia areata, vitiligo, ulcerative colitis, Crohn's disease, psoriasis and rheumatoid arthritis.

Clinical studies were conducted with oral administration of PF-06651600-15 at two different doses (10 and 50 mg tablets) using the material sparing tablet (MST) formulation. The MST formulation contained excipients that were well understood in terms of generating a product with few manufacturing issues, including flow, compression/processability, ejection force, and punch adhesion, and could be used with a drug substances where the knowledge around the physical, mechanical and processing characteristics of the drug were not yet well understood. However, the MST formulation was found to be unstable as PF-06651600-15 readily underwent dimerization and oligomerization. In addition, a noticeable transformation in appearance was also observed for blends and tablets with samples turning from white to yellow/brown over time or exhibiting an intense localized color change. The poor stability profile necessitated the use of refrigerated storage and foil packaging.

Therefore, a need existed for the discovery of stable immediate release tablet or capsule formulations comprising PF-06651600-15 for administration of this compound to treat immune, autoimmune, and inflammatory disorders, in subjects.

SUMMARY OF THE INVENTION

The present invention provides a stable immediate release formulation comprising PF-06651600-15, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a method of treating an immune, autoimmune, or inflammatory disorder in a subject comprising administering to the subject in need of such treatment a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, including the para-toluenesulfonate salt, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

DETAILED DESCRIPTION OF THE INVENTION

Figure 1:
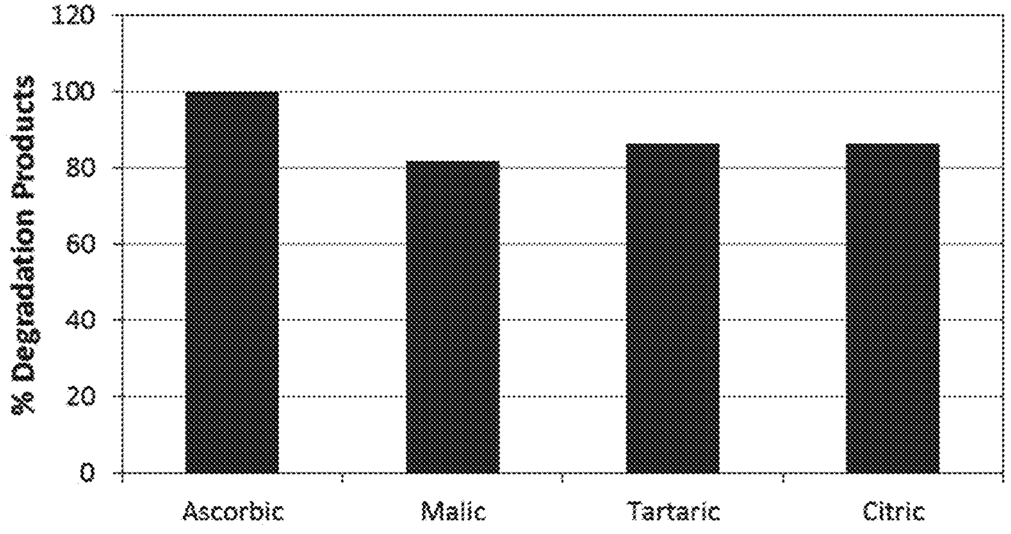
FIG. 1 provides stability data for PF-06651600-15 after combination with acids (proton donor excipients) at 1 week at 70° C./75% relative humidity (RH).

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the first filler is microcrystalline cellulose and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the second filler is lactose monohydrate and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the disintegrant is crospovidone (polyvinylpyrrolidone) and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one, or a pharmaceutically acceptable salt thereof, a first filler, a second filler, a disintegrant, and a glidant or lubricant, wherein the glidant or lubricant is glyceryl dibehenate and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, a first filler, a second filler, a disintegrant, and a glidant or lubricant, wherein the first filler is microcrystalline cellulose and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, a first filler, a second filler, a disintegrant, and a glidant or lubricant, wherein the second filler is lactose monohydrate and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, a first filler, a second filler, a disintegrant, and a glidant or lubricant, wherein the disintegrant is crospovidone (polyvinylpyrrolidone) and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, a first filler, a second filler, a disintegrant, and a glidant or lubricant, wherein the glidant or lubricant is glyceryl dibehenate and wherein the formulation has 0.7% w/w or less of a dimer of the 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, microcrystalline cellulose, lactose monohydrate, crospovidone, and glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, microcrystalline cellulose, lactose monohydrate, crospovidone, and glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, microcrystalline cellulose, lactose monohydrate, crospovidone, and glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising 1-((2S,5R)-5-((7H-pyrrolo[2,3-d]pyrimidin-4-yl)amino)-2-methylpiperidin-1-yl)prop-2-en-1-one para-toluenesulfonate salt, microcrystalline cellulose, lactose monohydrate, crospovidone, and glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising about 10-75% 1-((2S,5R)-5-((7H-pyrrolo[2,3-d]pyrimidin-4-yl)amino)-2-methylpiperidin-1-yl)prop-2-en-1-one para-toluenesulfonate salt, about 10-50% microcrystalline cellulose, about 10-50% lactose monohydrate, about 0.5-5% crospovidone; and about 1-15% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising about 10-75% 1-((2S,5R)-5-((7H-pyrrolo[2,3-d]pyrimidin-4-yl)amino)-2-methylpiperidin-1-yl)prop-2-en-1-one para-toluenesulfonate salt, about 10-50% microcrystalline cellulose, about 10-50% lactose monohydrate, about 0.5-5% crospovidone; and about 1-15% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising about 10-75% 1-((2S,5R)-5-((7H-pyrrolo[2,3-d]pyrimidin-4-yl)amino)-2-methylpiperidin-1-yl)prop-2-en-1-one para-toluenesulfonate salt, about 10-50% microcrystalline cellulose, about 10-50% lactose monohydrate, about 0.5-5% crospovidone; and about 1-15% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising about 10-75% 1-((2S,5R)-5-((7H-pyrrolo[2,3-d]pyrimidin-4-yl)amino)-2-methylpiperidin-1-yl)prop-2-en-1-one para-toluenesulfonate salt, about 10-50% microcrystalline cellulose, about 10-50% lactose monohydrate, about 0.5-5% crospovidone; and about 1-15% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising about 55-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-18% microcrystalline cellulose, about 12-18% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising about 55-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-18% microcrystalline cellulose, about 12-18% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising about 55-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-18% microcrystalline cellulose, about 12-18% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising about 55-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-18% microcrystalline cellulose, about 12-18% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising about 58-62% 1-((2S,5R)-5-((7H-pyrrolo[2,3-d]pyrimidin-4-yl)amino)-2-methylpiperidin-1-yl)prop-2-en-1-one para-toluenesulfonate salt, about 14-18% microcrystalline cellulose, about 14-18% lactose monohydrate, about 2-4% crospovidone; and about 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising about 58-62% 1-((2S,5R)-5-((7H-pyrrolo[2,3-d]pyrimidin-4-yl)amino)-2-methylpiperidin-1-yl)prop-2-en-1-one para-toluenesulfonate salt, about 14-18% microcrystalline cellulose, about 14-18% lactose monohydrate, about 2-4% crospovidone; and about 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising about 58-62% 1-((2S,5R)-5-((7H-pyrrolo[2,3-d]pyrimidin-4-yl)amino)-2-methylpiperidin-1-yl)prop-2-en-1-one para-toluenesulfonate salt, about 14-18% microcrystalline cellulose, about 14-18% lactose monohydrate, about 2-4% crospovidone; and about 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising about 58-62% 1-((2S,5R)-5-((7H-pyrrolo[2,3-d]pyrimidin-4-yl)amino)-2-methylpiperidin-1-yl)prop-2-en-1-one para-toluenesulfonate salt, about 14-18% microcrystalline cellulose, about 14-18% lactose monohydrate, about 2-4% crospovidone; and about 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo

[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,\ 0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet formulation comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.50 microns $D_{[\nu,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v, 0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,\ 0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,\ 0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop- 2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 47.08-49.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 11.76-13.76 mgs of microcrystalline cellulose, 11.76-13.76 mgs of lactose monohydrate, 1.90-2.90 mgs of crospovidone, and 3.50-4.50 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop- 2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop- 2-en-1-one and a total degradant product amount of 1.2% w/w or less at 0-60° C./10-40% relative humidity for at least 28 days.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 79.13-81.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 20.27-22.27 mgs of microcrystalline cellulose, 20.27-22.27 mgs of lactose monohydrate, 3.50-4.50 mgs of crospovidone, and 6.17-7.17 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]

pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release tablet comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 290 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 158.26-162.26 mgs of 1-((2S,5R)-5-((7H-pyrrolo[2,3-d]pyrimidin-4-yl)amino)-2-methylpiperidin-1-yl) prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-

5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 159.26-161.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 41.54-43.54 mgs of microcrystalline cellulose, 41.54-43.54 mgs of lactose monohydrate, 7.50-8.50 mgs of crospovidone, and 12.83-13.83 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-60° C./10-40% relative humidity for at least 28 days.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-75% relative humidity for at least six months.

In another embodiment, the present invention provides a stable immediate release formulation in a HPMC capsule comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating an immune, autoimmune, or inflammatory disorder in a subject comprising administering to the subject in need of such treatment any of the stable immediate release formulations described herein. In particular, the stable immediate release formulations described herein may be used to treat alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a tablet or capsule comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a tablet or capsule comprising about 58-62% 1-((2S,5R)-5-((7H-pyrrolo[2,3-d]pyrimidin-4-yl)amino)-2-methylpiperidin-1-yl)prop-2-en-1-one para-toluenesulfonate salt, about 14-18% microcrystalline cellulose, about 14-18% lactose monohydrate, about 2-4% crospovidone; and about 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a tablet or capsule comprising about 55-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-18% microcrystalline cellulose, about 12-18% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a tablet or capsule comprising 58-62% 1-((2S,5R)-5-((7H-pyrrolo[2,3-d]pyrimidin-4-yl)amino)-2-methylpiperidin-1-yl)prop-2-en-1-one para-toluenesulfonate salt, 14-18% microcrystalline cellulose, 14-18% lactose monohydrate, 2-4% crospovidone; and 3-8% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a 30 mg dose as a tablet or capsule comprising 46.08-50.08 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 10.76-14.76 mgs of microcrystalline cellulose, 10.76-14.76 mgs of lactose monohydrate, 1.40-3.40 mgs of crospovidone, and 3.00-5.00 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt is unmilled, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment one or more 30 mg dose capsules comprising 48.077 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 12.762 mgs of microcrystalline cellulose, 12.762 mgs of lactose monohydrate, 2.400 mgs of crospovidone, and 4.000 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a 50 mg dose as a tablet or capsule comprising 78.13-82.13 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 19.27-23.27 mgs of microcrystalline cellulose, 19.27-23.27 mgs of lactose monohydrate, 3.00-5.00 mgs of crospovidone, and 5.67-7.67 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment one or more 50 mg dose capsules comprising 80.128 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 21.269 mgs of microcrystalline cellulose, 21.269 mgs of lactose monohydrate, 4.000 mgs of crospovidone, and 6.667 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment a 100 mg dose as a tablet or capsule comprising 158.26-162.26 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 40.54-44.54 mgs of microcrystalline cellulose, 40.54-44.54 mgs of lactose monohydrate, 7.00-9.00 mgs of crospovidone, and 12.33-14.33 mgs of glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

In another embodiment, the present invention provides a method of treating alopecia areata, vitiligo, inflammatory bowel disease, irritable bowel syndrome, Crohn's disease, ulcerative colitis, rheumatoid arthritis, osteoarthritis, juvenile idiopathic arthritis, psoriatic arthritis, ankylosing spondylitis, psoriasis, plaque psoriasis, allergic dermatitis, hidradenitis suppurativa, lupus nephritis, or systemic lupus erythematosus in a subject comprising administering to the subject in need of such treatment one or more 100 mg dose capsules comprising 160.256 mgs of 1-((2S,5R)-5-((7H-pyrrolo[2,3-d]pyrimidin-4-yl)amino)-2-methylpiperidin-1-yl)prop-2-en-1-one para-toluenesulfonate salt, 42.539 mgs of microcrystalline cellulose, 42.539 mgs of lactose monohydrate, 8.000 mgs of crospovidone, and 13.333 mgs of glyceryl dibehenate, wherein the 1-((2S,5R)-5-((7H-pyrrolo[2,3-d]pyrimidin-4-yl)amino)-2-methylpiperidin-1-yl)prop-2-en-1-one para-toluenesulfonate salt has particle size 300.5 microns $D_{[v,0.9]}$, and wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one and a total degradant product amount of 1.2% w/w or less at 0-30° C./10-65% relative humidity for at least one year.

The term "about," as used herein, means±2.5.

The term "acceptable criteria," as used herein, means that the acceptable amount of dimer is 0.7% w/w and the acceptable amount of total degradant products is 1.2% w/w wherein total degradant formation includes the amount of dimer.

The term "material sparing tablet formulation" or "MST formulation" or "MST tablet," or "lot 16-002785" or "16-002785," as used herein, means the tablets or formulation used in the phase II studies comprising: 16.05% PF-06651600-15 (10.00% active amount); 53.30% microcrystalline cellulose; 26.65% di-calcium phosphate, 3.00% sodium starch glycolate (explotab); and 1.00% magnesium stearate. The 100 mg MST tablet was comprised of: 16.051 mgs PF-06651600-15 (10 mgs API); 53.299 mgs microcrystalline cellulose; 26.650 mgs di-calcium phosphate, 3.000 mgs sodium starch glycolate (explotab); 0.500 intra-granular magnesium stearate; and 0.500 extra-granular magnesium stearate. The 500 mg MST tablet was comprised of: 80.257 mgs PF-06651600-15 (50 mgs API); 266.543 mgs microcrystalline cellulose; 133.200 mgs di-calcium phosphate, 15.000 mgs sodium starch glycolate (explotab); 2.500 intra-granular magnesium stearate; and 2.500 extra-granular magnesium stearate.

The term "PF-06651600" or "active" or "active pharmaceutical agent" or "API" or "drug product," as used herein, means 1-((2S,5R)-5-((7H-Pyrrolo[2,3-d]pyrimidin-4-yl)amino)-2-methylpiperidin-1-yl)prop-2-en-1-one and includes any pharmaceutically acceptable crystalline or amorphous form including hydrates, solvates, co-crystals, salts and combinations thereof.

Certain forms may be prepared following the experimental procedures disclosed in WO2015/083028 and Thorarensen et al., J. Med. Chem. 2017, 60, 1971-1993, both documents are herein incorporated by reference in their entirety.

The term "PF-06651600-15," as used herein, means 1-((2S,5R)-5-((7H-Pyrrolo[2,3-d]pyrimidin-4-yl)amino)-2-methylpiperidin-1-yl)prop-2-en-1-one para-toluenesulfonate salt having structure

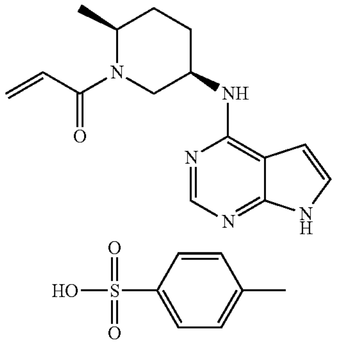

and includes any pharmaceutically acceptable crystalline or amorphous form including hydrates, solvates, co-crystals and combinations thereof. Certain forms of the 1-((2S,5R)-5-((7H-Pyrrolo[2,3-d]pyrimidin-4-yl)amino)-2-methylpiperidin-1-yl)prop-2-en-1-one para-toluenesulfonate salt may be prepared following the experimental procedures described herein and in U.S. Ser. No. 62/748,628 and PCT/IB2019/058940, both documents are herein incorporated by reference in their entirety. In the formulations described herein, approximately 62.4% of the salt is active agent w/w PF-06651600.

The term "PF-06757444" or "dimer" as used herein, means 1-((2S,5R)-5-((1-(3-((2S,5R)-5-((7H-pyrrolo[2,3-d]pyrimidin-4-yl)amino)-2-methylpiperidin-1-yl)-3-oxopropyl)-1H-pyrrolo[2,3-d]pyrimidin-4-yl)amino)-2-methylpiperidin-1-yl)prop-2-en-1-one having structure

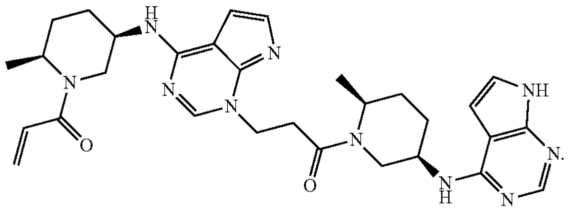 [SMILES: C=CC(=O)N1C[C@H](Nc2ncn(CCC(=O)N3C[C@H](Nc4ncnc5[nH]ccc45)CC[C@@H]3C)c3nccc2-3)CC[C@@H]1C]

The dimer was determined to be the main degradation product in the MST tablets. It is to be understood that the definition of dimer, as used herein, includes one or more dimers of 1-((2S,5R)-5-((7H-pyrrolo[2,3-d]pyrimidin-4-yl)amino)-2-methylpiperidin-1-yl)prop-2-en-1-one. For example, the three structures shown below are also dimers of 1-((2S,5R)-5-((7H-pyrrolo[2,3-d]pyrimidin-4-yl)amino)-2-methylpiperidin-1-yl)prop-2-en-1-one.

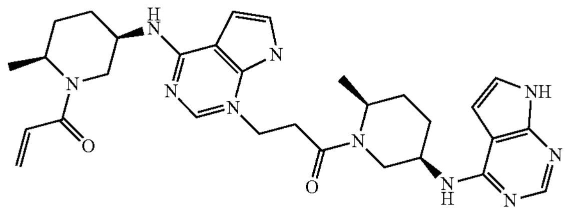

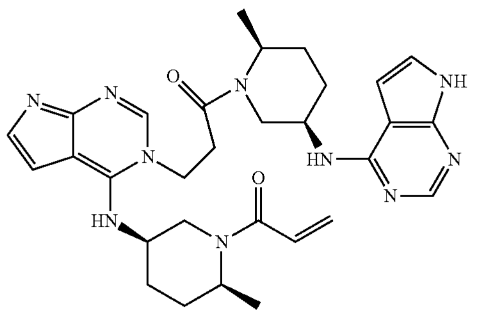

-continued

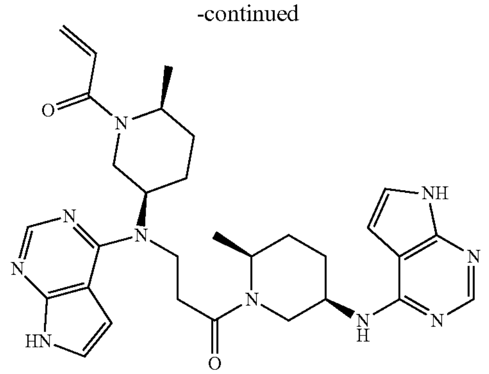

In particular, the term "a dimer," as used herein, includes one or more dimers of 1-((2S,5R)-5-((7H-pyrrolo[2,3-d]pyrimidin-4-yl)amino)-2-methylpiperidin-1-yl)prop-2-en-1-one.

The term "stable" or "stable immediate release formulation" or "stable immediate release tablet formulation" or "stable immediate release formulation in a HPMC capsule," as used herein, means the amount of dimer formation in the immediate release formulation is 0.7% w/w or less and the amount of total degradant products formed, including dimer, in the formulation is 1.2% w/w or less determined at certain temperatures, relative humidity, and time periods. For example, the language "wherein dimer formed is 0.7% or less and wherein total degradant products formed is 1.2% or less at 0-30° C./10-65% relative humidity for at least one year," as used herein, means that dimer formation is 0.7% or less w/w under the conditions of 0-30° C./10-65% relative humidity for at least one year and the total amount of degradant products, including the dimer, is 1.2% w/w or less under the conditions of 15-30° C./10-65% relative humidity for at least one year.

The term "subject" or "patient" or "individual," as used interchangeably herein, refers to a human or animal to which the methods of the present invention can be applied. In certain preferred embodiments, the subject is a human.

The term "w/w," as used herein, means weight for weight or weight by weight.

Preparation of 1-((2S,5R)-5-((7H-Pyrrolo[2,3-d]pyrimidin-4-yl)amino)-2-meth-ylpiperidin-1-yl)prop-2-en-1-one para-toluenesulfonate salt (A) To a 50 mL EasyMax™ flask equipped with an overhead stirrer, p-toluenesulfonic acid monohydrate (7.01 mmol, 1.35 g), methyl ethyl ketone (10.0 mL) and water (0.30 mL) were added. The solution was stirred at 22° C. for 5 min. A solution of 1-((2S,5R)-5-((7H-pyrrolo[2,3-d]pyrimidin-4-yl)amino)-2-methylpiperidin-1-yl)prop-2-en-1-one (7.01 mmol, 2.00 g) in methyl ethyl ketone (10.0 mL) was added slowly via addition funnel over 20 min. The slurry was stirred at 22° C. for 30 min. Methyl ethyl ketone (10.0 mL) was added slowly via addition funnel over 15 min. The slurry was stirred at 22° C. for 60 min. and then filtered. The solid was washed with methyl ethyl ketone (2×3 mL) and dried in a vacuum oven (30° C.) for 16 hours. 1-((2S,5R)-5-((7H-Pyrrolo[2,3-d]pyrimidin-4-yl)amino)-2-methylpiperidin-1-yl)prop-2-en-1-one p-toluene-sulfonic acid salt (Form 1) (5.81 mmol, 2.66 g) was obtained as a white sandy powder in 82.9% yield.

(B) A solution of p-toluenesulfonic acid monohydrate (2.66 g, 13.8 mmol) in methyl ethyl ketone (7.2 mL) was added to a stirred solution of 1-((2S,5R)-5-((7H-pyrrolo[2, 3-d]pyrimidin-4-yl)amino)-2-methylpiperidin-1-yl)prop-2-en-1-one (3.60 g, 12.5 mmol) in methyl ethyl ketone (22.5 mL) and water (1.56 mL) at 22° C. The seed of PF-06651600-15 (89 mg) was added and the mixture was stirred at 22° C. for 4 hours. Methyl ethyl ketone (48 mL) was then slowly added over a period of 1 hour. The slurry was stirred at 22° C. for 18 hours and then filtered. The cake was washed with methyl ethyl ketone (15 mL) and then dried under vacuum at 40° C. for 4 hours. 1-((2S,5R)-5-((7H-Pyrrolo[2,3-d]pyrimidin-4-yl)amino)-2-methylpiperidin-1-yl)prop-2-en-1-one p-toluenesulfonic acid salt (4.95 g, 10.8 mmol) was obtained as a white solid in 86% yield.

Formulation Data

The current formulation has been shown to be unstable with PF-06651600-15 readily undergoing dimerization and oligomerization within the drug product. A noticeable transformation in appearance is also observed for blends and tablets with samples turning from white to brown over time or exhibiting an intense localized color change.

An excipient compatibility screen was initiated to determine which constituents were driving the instability of the MST formulation and to evaluate the impact of alternative excipients on the chemical and physical stability of PF-06651600-15. Samples were prepared as individual binary mixes (i.e. 50% excipient to 50% PF-06651600-15) and stored for 1 week at 70° C./75% RH (relative humidity), after which the blend was assessed for color change and assayed to determine product impurities.

Samples were prepared in size 8 glass dram vials via the following steps: (1) weigh ~1 g of excipient into an 8 dram glass vial; (2) add ~1.6 g of PF-06651600-15 (~1 gram active agent) into the glass vial; and (3) close the vial and blend the components in a Turbula mixer at ~46-49 rpm for 10 minutes. The samples were stored at 70° C./75% RH for one week. These conditions were chosen to study the impact of high humidity known to affect the stability of the MST formulation. The focus was on appearance of the samples and amount of degradation products (as % total area).

The degradation and color change observed with the MST formulation was thought to be primarily driven by disproportionation of PF-06651600 and para-toluene sulfonic acid. In order to determine whether disproportionation of PF-06651600-15 resulted in degradation, experiments were conducted lowering the pH of the formulation below the $pH_{max}$ value of PF-06651600-15. Samples were prepared with PF-06651600-15 in the presence of a range acids or proton donors. All of the PF-06651600-15 blends prepared with a proton donor demonstrated high levels of degradation product formation (>80%) after one-week storage at 70° C./75% relative humidity (FIG. 1). This was also accompanied by a significant change in the appearance of all samples from a white powder to an orange deliquescent (Table 1) demonstrating that these acids were hygroscopic. These results suggested that PF-06651600-15 was incompatible with high concentrations of acid (low pH micro-environment) and/or hygroscopic excipients in the mixtures.

Figure 2:
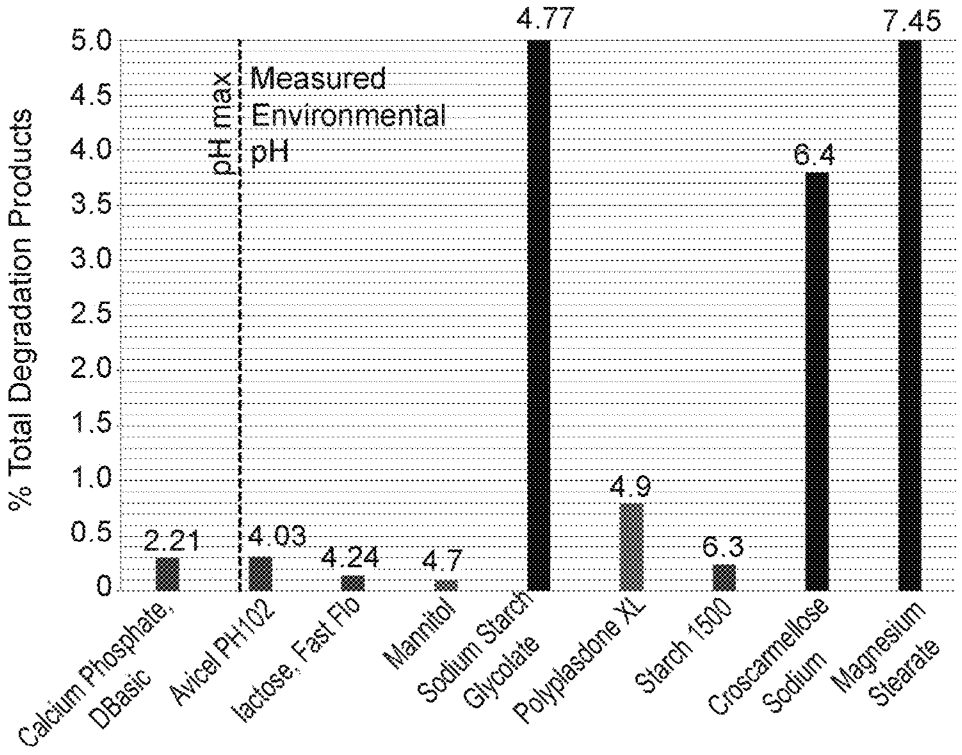
FIG. 2 provides stability data for PF-06651600-15 after combination with excipients ranked by micro-environmental pH at 1 week at 70° C./75% RH.
Figure 3:
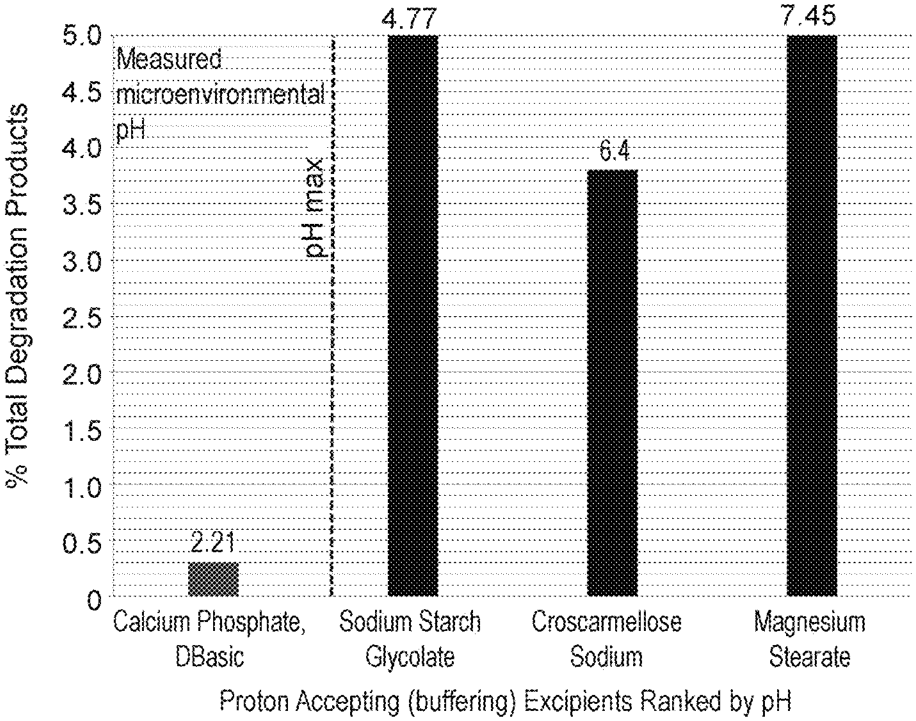
FIG. 3 provides stability data for PF-06651600-15 after combination with proton acceptor excipients at 1 week at 70° C./75% RH.

To further explore the effect the micro-environment pH has on degradation of PF-06651600-15, several excipients were combined with PF-06651600-15 and stored for 1 week at 70° C./75% RH (FIGS. 2 and 3). The excipients containing a proton accepting carboxylate with a pH above the $pH_{max}$ of the tosylate salt (magnesium stearate, sodium starch glycolate, croscarmellose sodium) induced a noticeable color change (Table 1) in the appearance of the binary mixture. In addition, these excipients were accompanied by an elevation in the amount of degradation products within the final sample. The carboxylate groups present in these excipients are capable of accepting a proton from the salt which may facilitate disproportionation. Unexpectedly, di-basic calcium phosphate, also capable of accepting a proton, did not induce a significant amount of color change or degradation. These results demonstrated that degradation of PF-06651600-15 due to excipient contact was unpredictable and also that the excipient micro-environmental pH alone may not explain the instability of PF-06651600-15.

Figure 4:
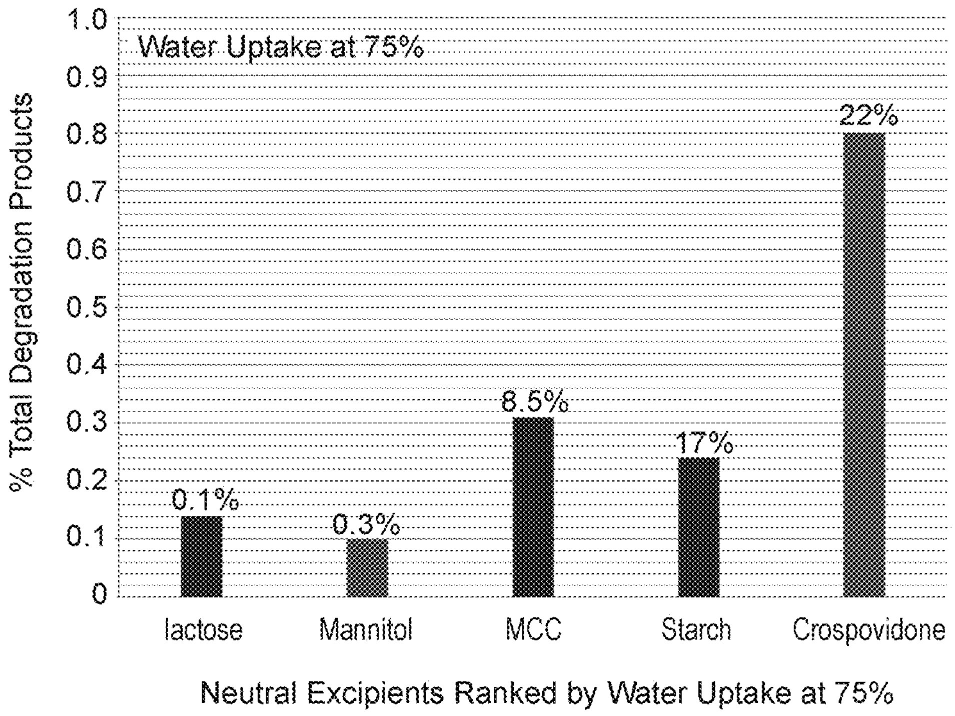
FIG. 4 provides stability data for PF-06651600-15 after combination with neutral hygroscopic excipients after 1 week at 70° C./75% RH.

Hygroscopic excipients have the ability to uptake water and deliquesce above a critical relative humidity which may facilitate color change and an increase in degradation levels of PF-06651600-15 (FIG. 4). Hygroscopic excipients may enhance the rate of disproportionation, and hence degradation of PF-06651600-15, as water facilitates the change in ionization via proton transfer.

Figure 5:
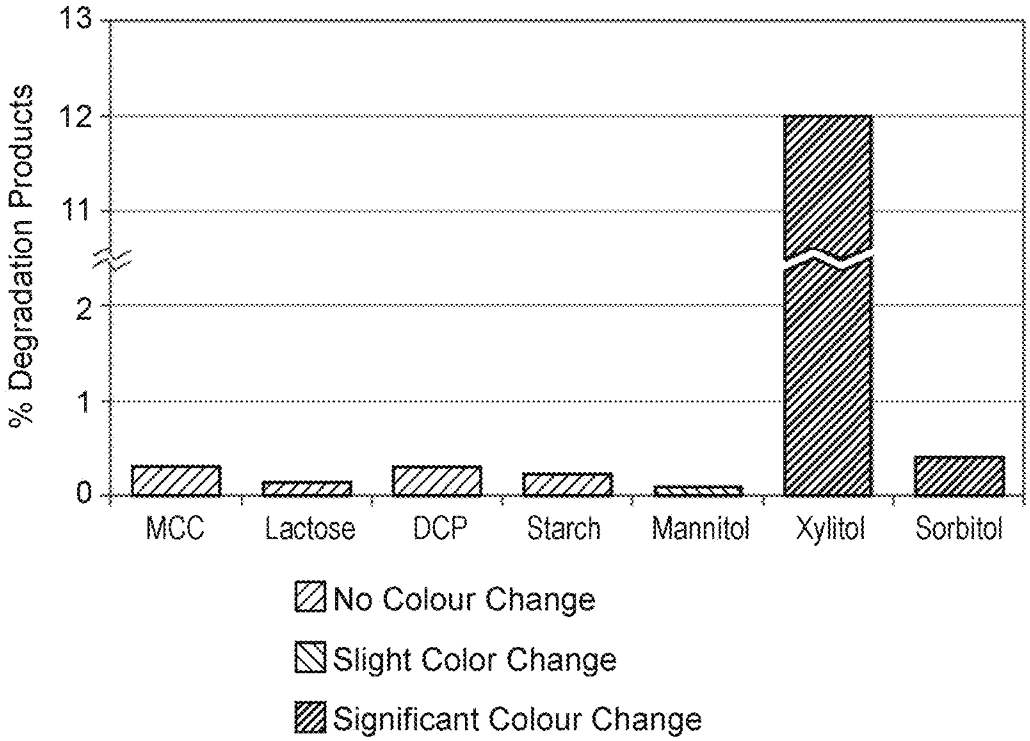
FIG. 5 provides stability data for PF-06651600-15 after combination with filler excipients at 1 week at 70° C./75% RH.
Figure 6A:
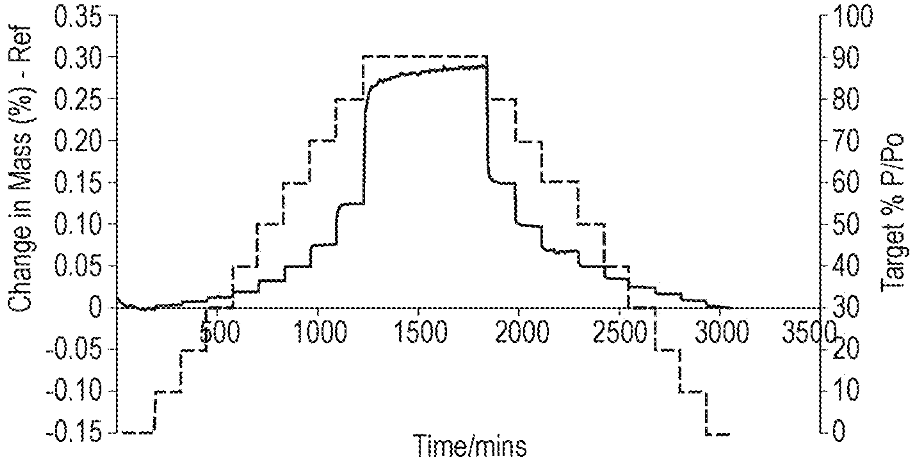
FIG. 6 provides dynamic vapor sorption (DVS) traces for mannitol and xylitol.
Figure 6B:
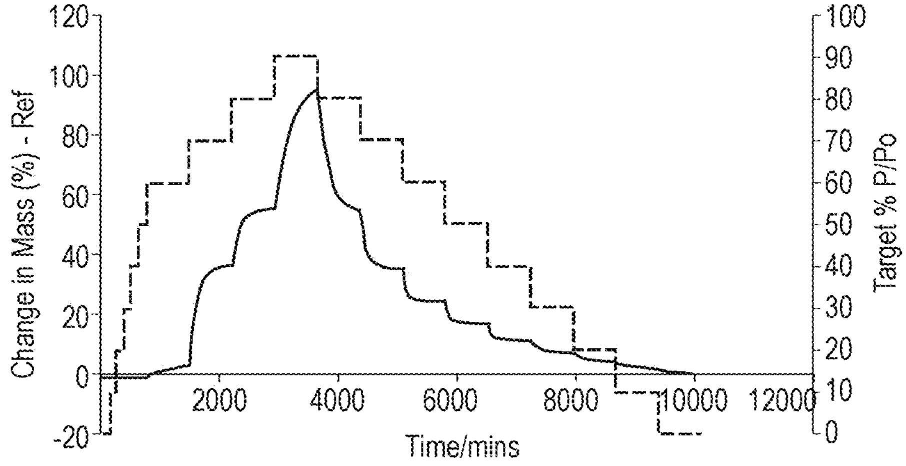

The stability of PF-06651600-15 was studied with a range of fillers (FIG. 5) including microcrystalline cellulose (Avicel PH102), lactose monohydrate, di-basic calcium phosphate and starch, all of which exhibited no color change and degradant product formation was lower than 1%. Mannitol showed a slight change in the color of the blend (off-white to brown) but demonstrated a high level of chemical stability. A significant localised color change was observed with sorbitol (off-white to orange) despite a low level (<1%) of generated degradant. Xylitol demonstrated both poor chemical stability (12% degradation) and a significant change in appearance (off-white to yellow) throughout the sample. A dynamic vapor sorption (DVS) plot was generated for both mannitol and xylitol (FIG. 6) that showed mannitol had low uptake of water whereas xylitol was found to be hygroscopic suggesting that water may contribute to the degradation of PF-06651600-15.

Figure 7:
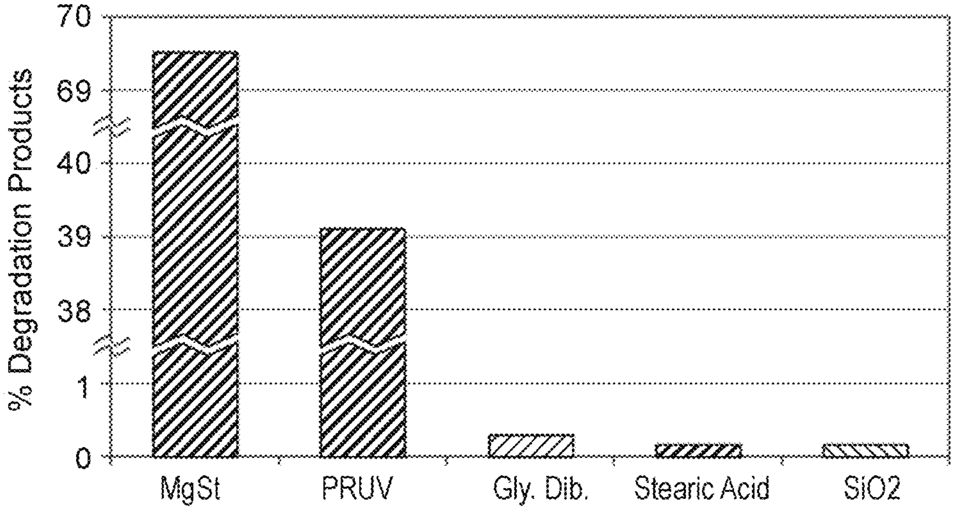
FIG. 7 provides stability data for PF-06651600-15 after combination with lubricant/glidant excipients at 1 week at 70° C./75% RH.

PF-06651600-15 was combined with a range of dry powder lubricants (FIG. 7). Magnesium stearate and sodium stearyl fumarate (PRUV) exhibited a high level of chemical degradation accompanied by a noticeable change in the appearance of the sample. Magnesium stearate turned from off-white to red/brown and PRUV turned from off-white to orange/brown. The remaining lubricants and glidants (glyceryl dibehenate, stearic acid, silicon dioxide) tested showed acceptable chemical stability with PF-06651600-15 with degradation product formation at less than 1% when stored at 70C/75% RH for 1 week. Stearic acid produced a noticeable localized change in the appearance of the sample, glyceryl dibehenate showed a slight coloring (off-white to light yellow), and silicon dioxide did not change color. These results demonstrated that magnesium stearate, used in the MST formulation, was highly incompatible with PF-06651600-15 and therefore may have been a contributing factor to the recorded instability of the drug product. Silicon dioxide appeared to be an acceptable excipient for use within a PF-06651600-15 tablet formulation.

Figure 8:
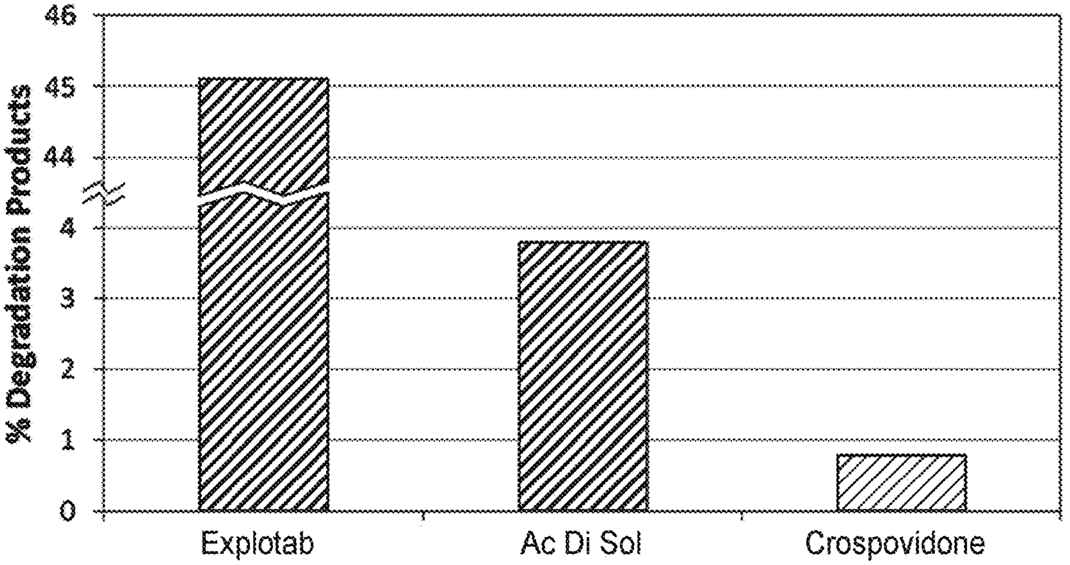
FIG. 8 provides stability data for PF-06651600-15 after combination with disintegrant excipients at 1 week at 70° C./75% RH.

The stability of PF-06651600-15 when combined with excipients to aid disintegration (FIG. 8) such as sodium starch glycolate (explotab), used in the MST formulation, exhibited degradant levels greater than 40%, turned color from off-white to yellow, and was deliquescent in appearance. Croscarmellose sodium (Ac-Di-Sol) exhibited levels of degradation products greater than 3% within the sample and a significant observed color change from off-white to light brown. The crospovidone (polyplasdone XL) blend exhibited chemical stability (<1%) with a slight yellowing of the powder.

The results demonstrated that PF-06651600-15 was incompatible with a wide range of excipients. In particular, high levels of degradation were observed when PF-06651600-15 was combined with acids and materials containing carboxylate groups (proton acceptors) suggesting that magnesium stearate and explotab contained within the MST formulation contributed to that formulation's instability issues. In addition, hygroscopic excipients such as xylitol when combined with PF-06651600-15 generated high levels of degradation products. Excipients found that may be suitable for combination with PF-06651600-15 included the fillers microcrystalline cellulose (MOO), lactose, di-calcium phosphate (DOP), mannitol, and starch; the lubricants/glidants glyceryl dibehenate and silicon dioxide; and the disintegrant crospovidone.

TABLE 1

Appearance of PF-06651600-15 After 1 Week Storage at 70° C./75% Relative Humidity

| Excipient type | Excipient | 5° C. (Control) | 1 week at 70° C./75% RH |
|---|---|---|---|
| Fillers | MCC | White to off-white powder | off-white powder |
| | Lactose | White to off-white powder | slight browning towards the vial glass wall |
| | DCP | White to off-white powder | slight browning towards the vial glass wall |
| | Starch | White to off-white powder | off-white powder |
| | Mannitol | White to off-white powder | localized brown deliquesced spots on the glass wall |
| | Xylitol | White to off-white powder | Severe yellowing |
| | Sorbitol | White to off-white powder | Strong localized orange coloration |
| Lubricants/Glidants | Magnesium Stearate | White to off-white powder | red/brown, non-homogenous coloration, localized white specks |
| | PRUV | White to off-white powder | orange/brown, non-homogenous coloration, localized white specks |
| | Glyceryl Dibehenate | White to off-white powder | Slight yellowing |
| | Stearic acid | White to off-white powder | Localized sites of strong coloration |
| | $SiO_2$ | White to off-white powder | White to off-white powder |
| Disintegrants | Explotab | White to off-white powder | yellow and deliquescent in appearance |
| | Ac-Di-Sol | White to off-white powder | light brown/off-white |
| | Crospovidone | White to off-white powder | Slight yellowing |
| Acids | Ascorbic | White to off-white powder | Orange and deliquescent in appearance |
| | Malic | White to off-white powder | Orange and deliquescent in appearance |
| | Tartaric | White to off-white powder | Orange and deliquescent in appearance |
| | Citric | White to off-white powder | Orange and deliquescent in appearance |

Based on the results of the excipient compatibility screen, the following excipients were used in various combinations with PF-06651600-15 to formulate immediate release experimental 50 mg tablets: microcrystalline cellulose (Avicel PH102); dibasic calcium phosphate anhydrous (A-TAB); pregelatinized corn starch (starch 1500); mannitol (perlitol 200 SD); lactose anhydrous; crospovidone (polyplasdone XL); glyceryl dibehenate (Compritol 888 ATO); colloidal silicon dioxide (Aerosil 200); and fumaric acid. Fumaric acid was not part of the excipient compatibility study but was identified as a non-hygroscopic acidifying agent which may enhance product stability by reducing the pH of the formulation. The formulations that were prepared, described in Table 2, contained 10% w/w active PF-06651600-15 with microcrystalline cellulose and a secondary filler in a 2:1 ratio, 5% w/w disintegrant (crospovidone) and 2% w/w lubricant (silicon dioxide or glyceryl dibehenate).

All blends in Table 2 were prepared via the following the steps:

1. Add the components to a suitably sized container in the following order:
   Microcrystalline Cellulose (Filler 1)
   PF-06651600-15
   Filler 2 (Mannitol, Lactose or Starch)
   Crospovidone (if required)
2. Blend the batch using a Turbula mixer for 5 minutes at 46 rpm
3. Screen the blend through a CoMill using an 813 micron mesh
4. Blend the resulting batch using a Turbula mixer for 5 minutes at 46 rpm
5. Screen the lubricant through an 800 micron sieve and add to the batch.
6. Blend the batch using a Turbula mixer for 2 minutes at 46 rpm Formulation F was a repeat of Formulation A except that silicon dioxide was substituted for glyceryl dibehenate to ascertain the impact on processing of the two different lubricants.

Formulation G was a repeat of formulation B except that 2% w/w fumaric acid was added at the end of step 1 of the blending process to determine the use of this excipient as a potential stabilizing agent.

TABLE 2

Experimental Tablet Formulations A-G

| Component | A (grams) | B (grams) | C (grams) | D (grams) | E (grams) | F (grams) | G (grams) |
|---|---|---|---|---|---|---|---|
| | Experimental Formulations | | | | | | |
| PF-06651600-15 | 24.10 | 24.07 | 24.09 | 24.09 | 24.05 | 12.04 | 24.08 |
| Microcrystalline Cellulose | 76.97 | 76.96 | 81.99 | 77.93 | 81.99 | 38.47 | 74.94 |
| Di-Calcium Phosphate | 38.49 | — | — | 39.00 | — | 19.24 | — |
| Starch | — | 38.45 | — | — | — | — | 37.47 |
| Mannitol | — | — | 40.96 | — | — | — | — |
| Crospovidone | 7.50 | 7.50 | — | 7.50 | — | 3.75 | 7.50 |
| Silicon Dioxide | 3.00 | | — | 1.50 | — | — | — |
| Glyceryl Dibehenate | — | 3.00 | 3.00 | — | 3.00 | 1.50 | 3.00 |
| Lactose Anhydrous | — | — | — | — | 40.96 | — | — |
| Fumaric Acid | — | — | — | — | — | — | 3.00 |
| Total | 150.06 | 149.98 | 150.04 | 150.02 | 150.00 | 75.00 | 149.99 |

Tablets were prepared using a Korsch XP1 tablet press to generate tablets under the following conditions: round 10 mm diameter src B-Type tooling; target tablet weight: 500 mg±4%; and target tablet crushing strength 10 kp. One hundred fifty tablets were produced from each batch to provide information on the physical properties of the tablet (weight, diameter, thickness and crushing strength) and to provide samples for drug product stability, dissolution testing, and solid-state stability. Tablet measurements were taken on three to four tablets throughout the run to ensure product consistency.

During the compression of the blends on the Korsch XP1, observations were made with regard to flow, processability (ease of compression), and punch adhesion. The ejection force value was taken directly from measurements made by the Korsch (Table 3).

These observations revealed that silicon dioxide could be used in small amounts to aid flow but cannot be used as a lubricant due to the high ejection forces recorded. In addition, the higher levels of silicon dioxide in formulation A affected the density of the blend leading to the compression and processability issues that were observed with Lot A as a result of the low bulk density of this formulation. The inclusion of glyceryl dibehenate, rather than $SiO_2$, reduced the ejection force. Of the four alternative fillers investigated (DCP, starch, mannitol and lactose) the mannitol blend was observed to exhibit poor flow (within the hopper) and had the greatest levels of punch adhesion.

TABLE 3

Summary of Compression Process Observations for Experimental Tablet Formulations A-G

| Formulation | Flow | Compression/ Processability | Ejection Force (N) | Punch Adhesion |
|---|---|---|---|---|
| A (MCC:DCP, 2% $SiO_2$) | Good | Moderate | 476 | Moderate |
| B (MCC:Starch) | Moderate | Good | 80 | Good |
| C (MCC:Mannitol) | Poor | Good | 109 | Poor |

TABLE 3-continued

Summary of Compression Process Observations for Experimental Tablet Formulations A-G

| Formulation | Flow | Compression/ Processability | Ejection Force (N) | Punch Adhesion |
|---|---|---|---|---|
| D (MCC:DCP, 1% $SiO_2$) | Good | Good | 770 | Poor |
| E (MCC:Lactose) | Moderate | Good | 137 | Poor |
| F (MCC:DCP, 2% dibehenate) | N/A | Good | 133 | Moderate |
| G (MCC:Starch + Fumaric acid) | Moderate | Good | 146 | Good |

Disintegration was assessed for lots A, B, C, E and G in 0.01 M HCl medium to ascertain whether the amount of disintegrant in tablets was suitable and in cases where no disintegrant was present whether the tablets disintegrate within an acceptable time. Disintegration results obtained on lots A, B, C, E and G are summarized and compared to that of the current formulation in Table 4. All batches disintegrated in less than thirty seconds, similar to the MST formulation. The lack of disintegrant in lots C and E did not have any adverse impact on the disintegration time of the tablets.

TABLE 4

Disintegration Times for Experimental Tablet Formulations A, B, C, E, and G Compared to the MST Formulation

| Lot | Run 1 (seconds) | Run 2 (seconds) | Run 3 (seconds) | Run 4 (seconds) | Run 5 (seconds) | Run 6 (seconds) | Maximum Disintegration (seconds) |
|---|---|---|---|---|---|---|---|
| Lot A | 11 | 15 | 15 | 11 | 15 | 11 | 15 |
| Lot B | 13 | 15 | 15 | 15 | 17 | 13 | 17 |
| Lot C | 11 | 11 | 11 | 13 | 11 | 15 | 15 |
| Lot E | 16 | 16 | 14 | 14 | 16 | 14 | 16 |
| Lot G | 16 | 20 | 18 | 20 | 16 | 26 | 26 |
| MST | 15 | 15 | 15 | 15 | 15 | 15 | 15 |

Figure 9A:
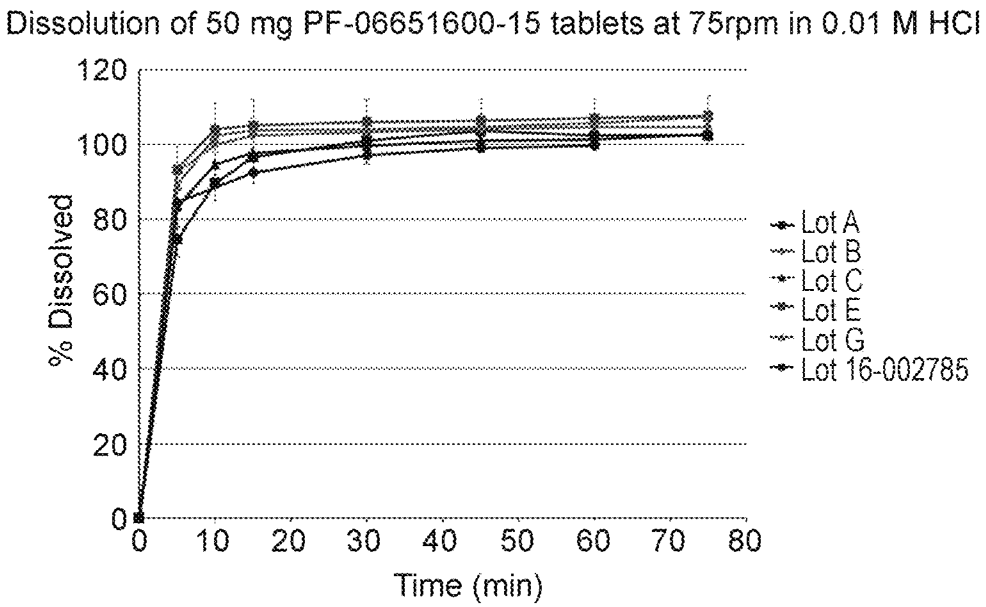
FIG. 9 provides dissolution data for the tablets prepared from experimental formulations A, B, C, E and G compared to the MST formulation at 75 rpm in 500 mL of 0.01 M HCl medium and 900 mL of pH 4.5 acetate medium.
Figure 9B:
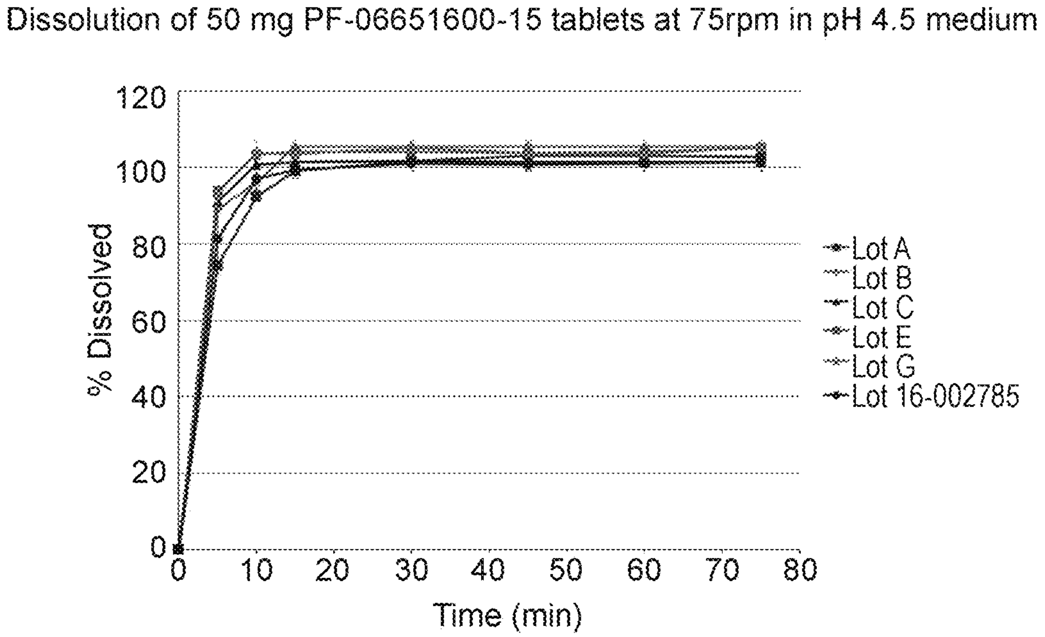

Dissolution was assessed for lots A, B, C, E and G at 75 rpm in 500 mL of 0.01 M HCl medium and 900 mL of pH 4.5 acetate medium (FIG. 9). The first set of conditions was chosen because that was the method used to monitor performance of the MST formulation. The second set was chosen as alternative conditions suitable to show discrimination between the batches. All batches disintegrated in less than a minute, similar to the MST formulation. The lack of disintegrant in lots C and E did not have any adverse impact on the disintegration time of the tablets.

Chemical stability was assessed under the Accelerated Stability Assessment Program (ASAP) conditions using high performance liquid chromatography with ultra-violet detection (HPLC-UV) analysis. Tablets from experimental lots A, B, C, E and G and from the MST formulation were stored under the conditions as stated in Table 5 with appearance and purity analysis performed at each time point. The level of degradation products as a percentage of total area was used to ascertain the stability of PF-06651600-15 within the formulation.

TABLE 5

ASAP Conditions

| Conditions | Duration (days) | |
|---|---|---|
| 5° C. | Control | |
| 50° C./75% RH* | 14 | 28 |
| 60° C./40% RH | 14 | 28 |
| 60° C./75% RH | 14 | 28 |
| 70° C./10% RH | 14 | 28 |
| 70° C./40% RH | 14 | 28 |
| 70° C./75% RH | 1 | 7 |
| 80° C./40% RH | 2 | 7 |

*RH means relative humidity

Figure 10:
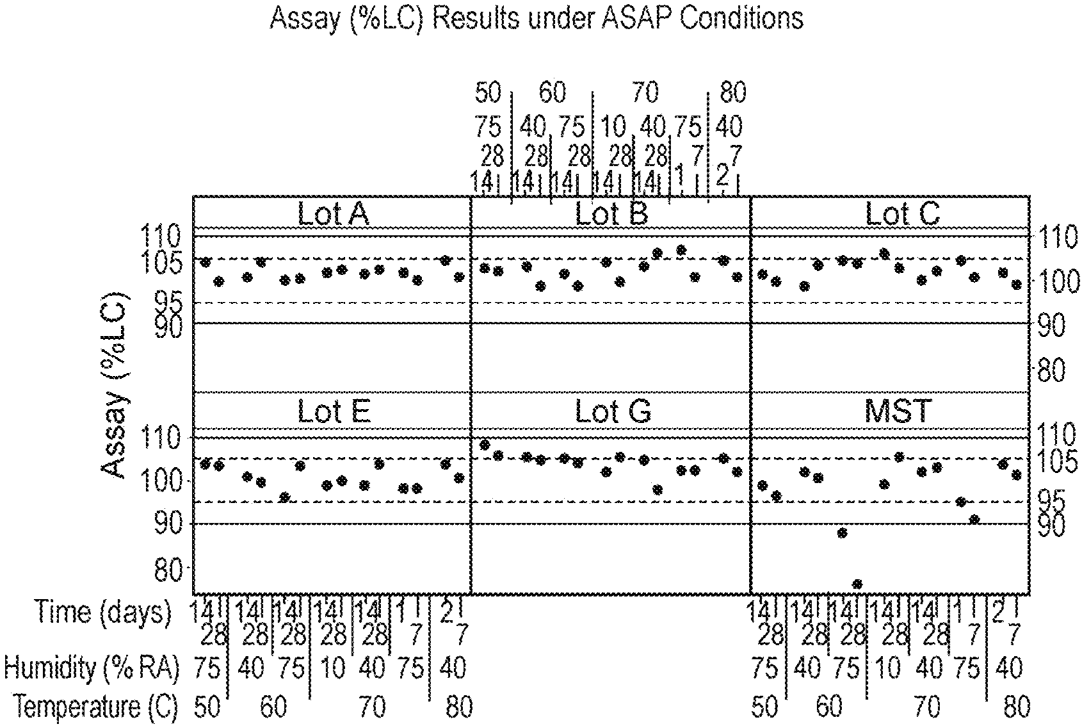
FIG. 10 provides degradation results for the tablets prepared from experimental formulations A, B, C, E, and G compared to the MST tablets under the Accelerated Stability Assessment Program (ASAP) conditions.

FIG. 10 summarizes the results for experimental lots A, B, C, E and G and the MST formulation when placed under ASAP conditions. The MST tablets stored at the highest relative humidity condition (75% RH) recorded the lowest ASAP values including the MST tablets stored for seven days at 70° C./75% RH and fourteen to twenty-eight days at 60° C./75% RH. This trend was not observed with the tablets from the experimental formulations as their ASAP values ranged between 95.0%-105.0%. Numerical ASAP values for the experimental lots are provided in Table 6 versus 5° C. control.

TABLE 6

ASAP Results for Experimental Tablet Formulations A, B, C, E, and G

| Conditions | Time | Experimental Formulations A | B | C | E | G |
|---|---|---|---|---|---|---|
| 5° C. control | | 102.9 | 109.0 | 103.8 | 105.1 | 103.3 |
| 50° C./75% RH | 14 days | 104.2 | 102.9 | 101.4 | 103.9 | 108.4 |
| | 28 days | 99.8 | 102.3 | 99.7 | 103.7 | 105.8 |
| 60° C./40% RH | 14 days | 100.7 | 103.1 | 98.7 | 101.1 | 105.4 |
| | 28 days | 104.3 | 98.6 | 103.4 | 99.6 | 104.8 |
| 60° C./75% RH | 14 days | 99.9 | 101.5 | 104.7 | 96.3 | 105.3 |
| | 28 days | 100.5 | 98.7 | 103.8 | 103.6 | 104.3 |
| 70° C./10% RH | 14 days | 101.8 | 104.2 | 106.1 | 99.0 | 102.0 |
| | 28 days | 102.5 | 99.6 | 102.7 | 100.1 | 105.5 |
| 70° C./40% RH | 14 days | 101.5 | 103.1 | 100.2 | 99.1 | 104.8 |
| | 28 days | 102.5 | 106.2 | 102.1 | 103.7 | 98.0 |
| 70° C./75% RH | 1 day | 101.9 | 106.9 | 104.5 | 98.4 | 102.5 |
| | 7 days | 100.2 | 100.7 | 100.6 | 98.3 | 102.6 |

TABLE 6-continued

ASAP Results for Experimental Tablet Formulations A, B, C, E, and G

| Conditions | Time | Experimental Formulations A | B | C | E | G |
|---|---|---|---|---|---|---|
| 80° C./40% RH | 2 days | 104.5 | 104.4 | 101.9 | 104.0 | 105.3 |
| | 7 days | 100.9 | 100.8 | 99.0 | 100.7 | 102.0 |

Figure 11A:
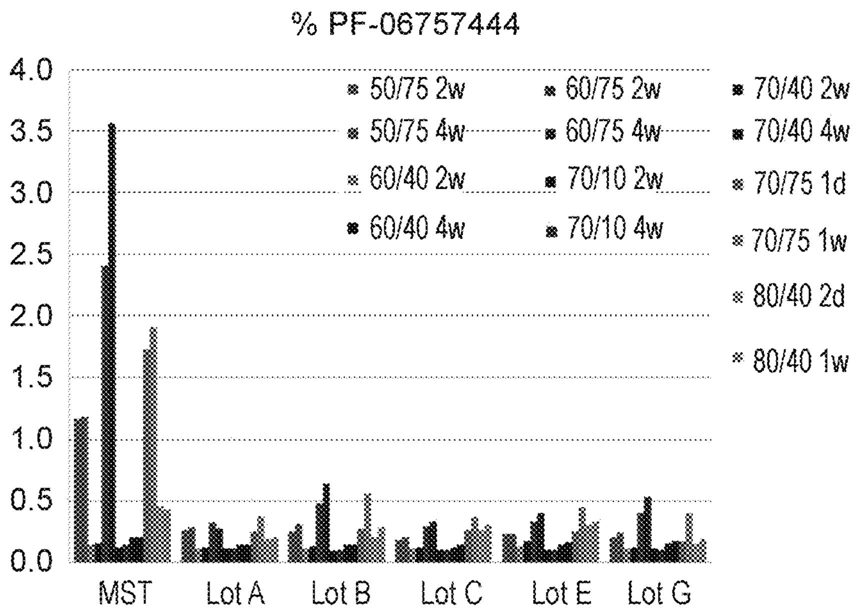
FIG. 11 provides the percent dimerization of PF-06651600-15 (top) and the percent of total degradation (bottom) of PF-06651600-15 for the tablets prepared from experimental formulations A, B, C, E, and G compared to the MST formulation under ASAP conditions.
Figure 11B:
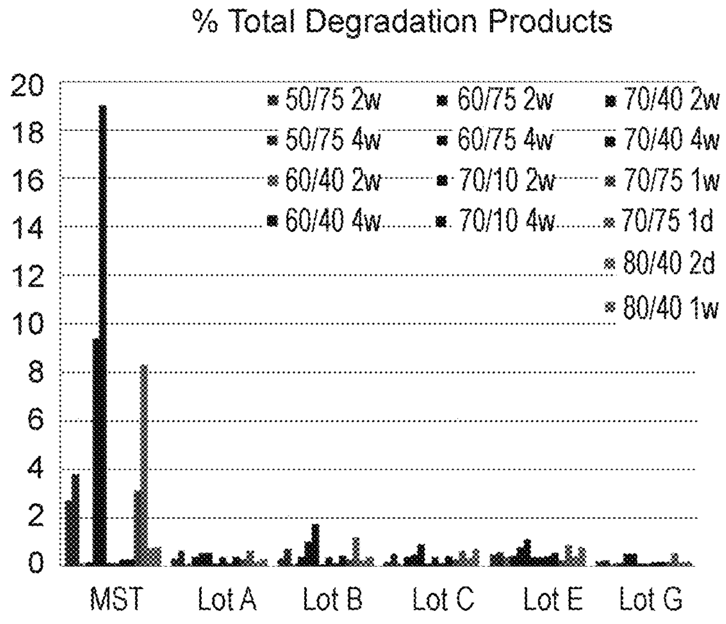
Figure 12:
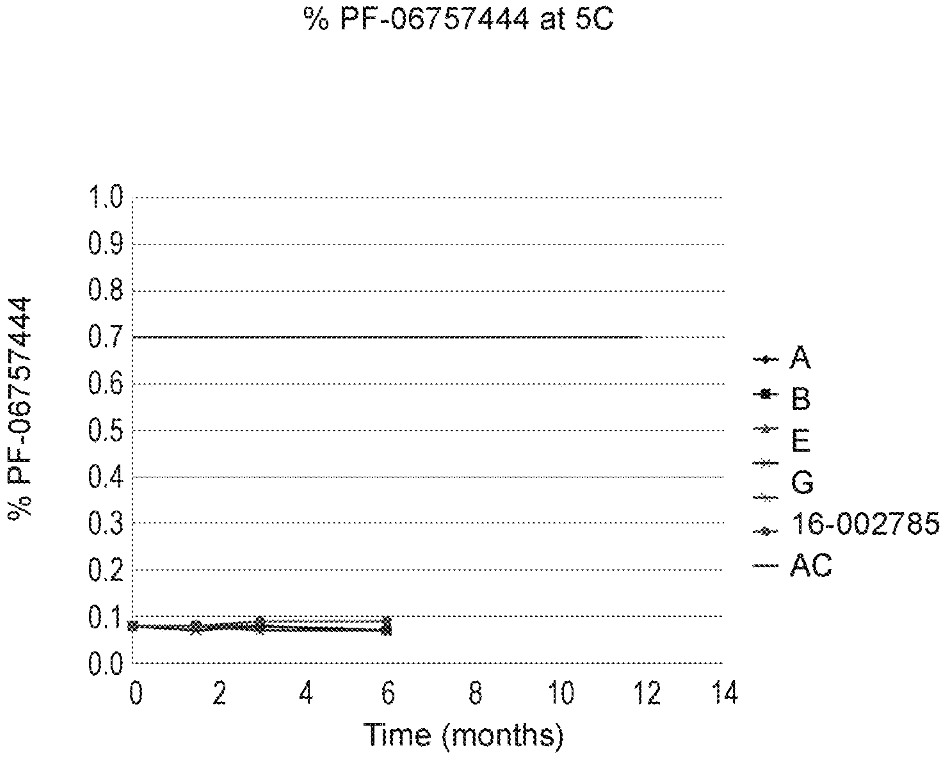
FIG. 12 provides the percentage of dimer detected in tablets prepared from the experimental formulations A, B, C, E, and G and in the MST tablets at 5° C. in an open dish over a six-month period. AC means acceptable concentration of dimer (0.7%). 16-002785 is the MST formulation.
Figure 13:
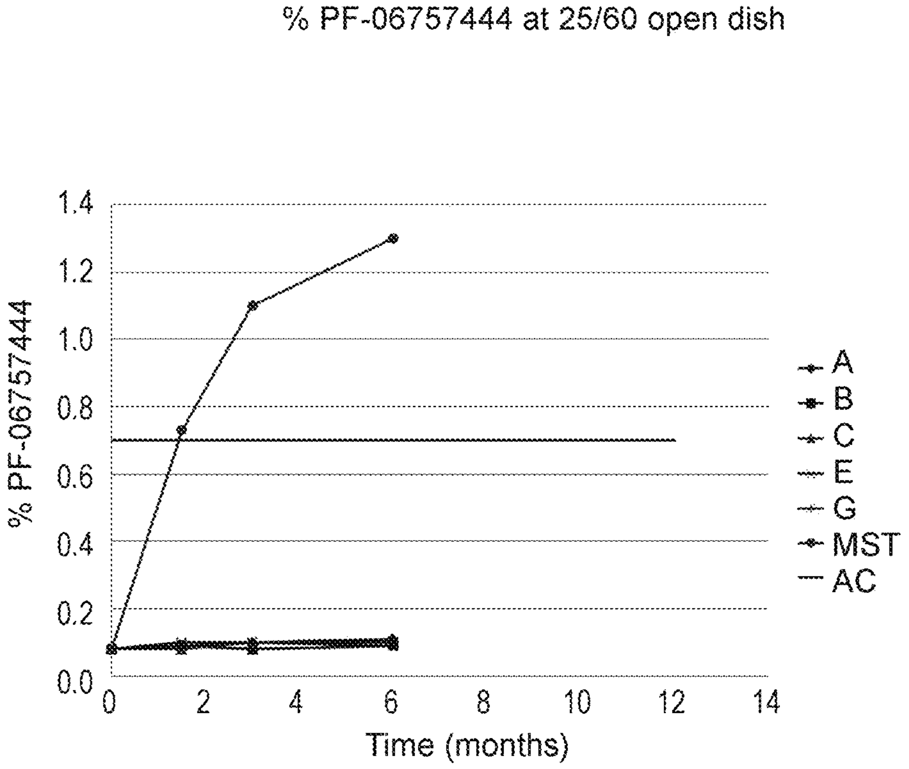
FIG. 13 provides the percentage of dimer detected in tablets prepared from the experimental formulations A, B, C, E, and G and in the MST tablets at 25° C./60% RH in an open dish over a six-month period.
Figure 14:
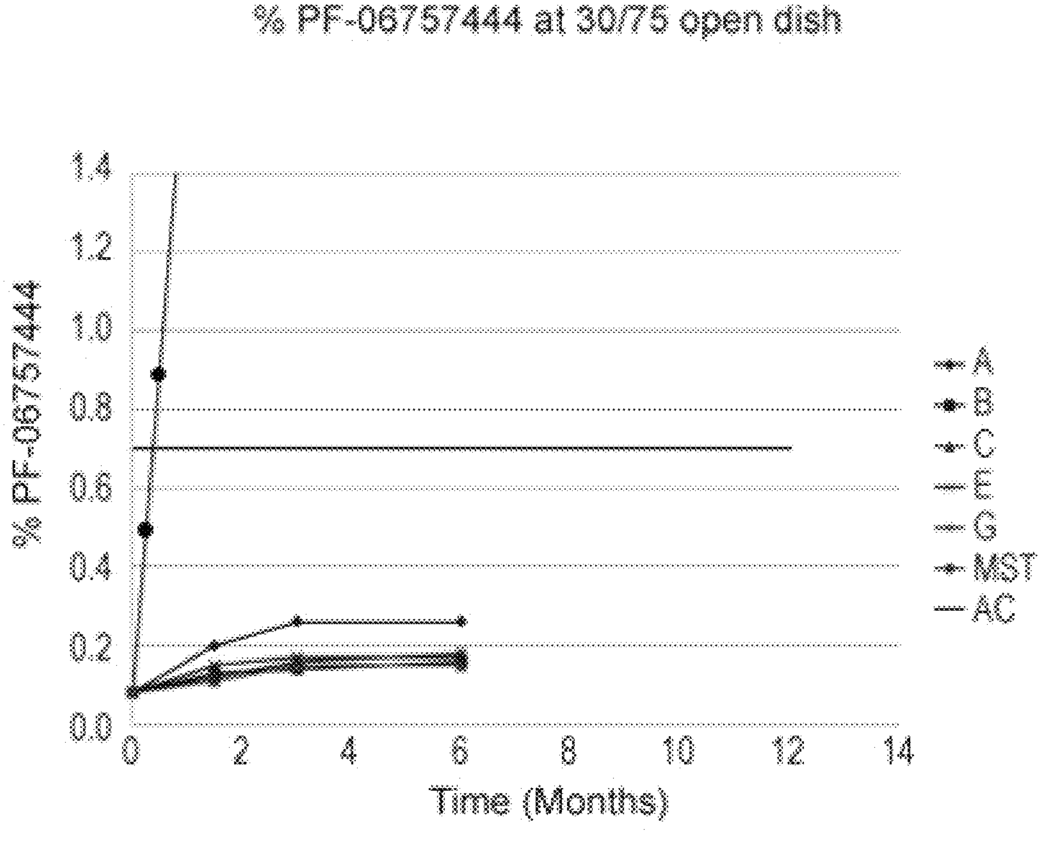
FIG. 14 provides the percentage of dimer detected in tablets prepared from the experimental formulations A, B, C, E, and G and in the MST tablets at 30° C./75% RH in an open dish over a six-month period. AC means acceptable concentration of dimer (0.7%).
Figure 15:
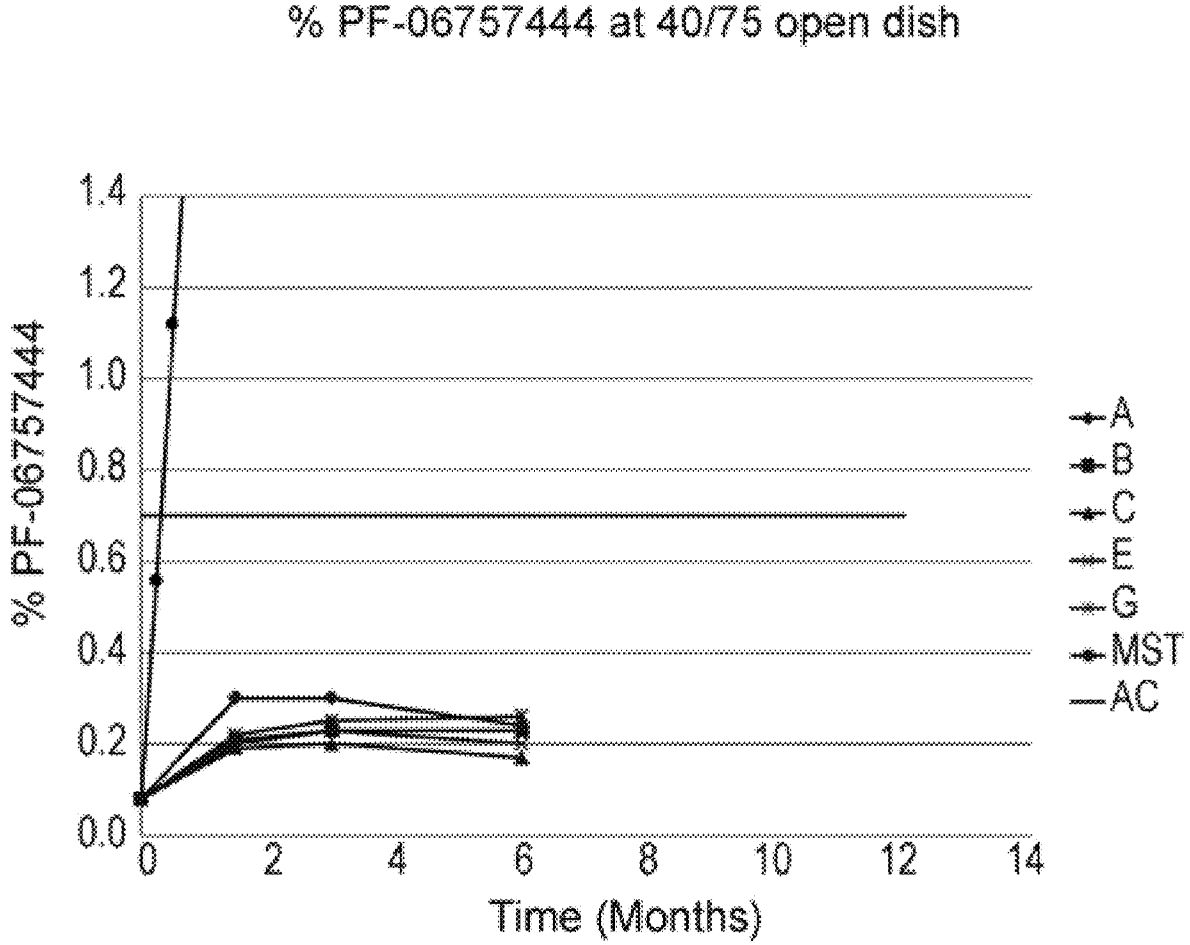
FIG. 15 provides the percentage of dimer detected in tablets prepared from the experimental formulations A, B, C, E, and G and in the MST tablets at 40° C./75% RH in an open dish over a six-month period. AC means acceptable concentration of dimer (0.7%).

FIG. 11 compares the percentage of dimer and the percentage of total degradation products detected for the tablets prepared from experimental formulations A, B, C, E, and G and for the MST tablets subjected to ASAP conditions. An improvement in the stability of the experimental tablets was observed particularly at the highest relative humidity (75% RH) where significantly lower levels of degradation was observed for the experimental formulations.

Table 7 provides a numerical comparison of the percentages of dimer and total degradation products detected for tablets prepared from experimental formulations A, B, C, E, and G that were subjected to ASAP conditions between one and twenty-eight days.

TABLE 7

Degradation Results for Experimental Tablets A, B, C, E, and G Under ASAP Conditions Between 1 and 28 Days

| Conditions | Time | Impurities | Experimental Tablet Formulations A | B | C | E | G |
|---|---|---|---|---|---|---|---|
| 5° C. | | % Dimer | 0.09 | 0.08 | 0.07 | 0.07 | 0.08 |
| | | % Total Deg. Prod. | 0.09 | 0.08 | 0.07 | 0.07 | 0.08 |
| 50° C./75% RH | 14 days | % Dimer | 0.26 | 0.25 | 0.18 | 0.23 | 0.20 |
| | | % Total Deg. Prod. | 0.32 | 0.31 | 0.18 | 0.23 | 0.20 |
| | 28 days | % Dimer | 0.28 | 0.31 | 0.20 | 0.23 | 0.24 |
| | | % Total Deg. Prod. | 0.36 | 0.43 | 0.27 | 0.30 | 0.24 |
| 60° C./40% RH | 14 days | % Dimer | 0.11 | 0.11 | 0.11 | 0.13 | 0.11 |
| | | % Total Deg. Prod. | 0.11 | 0.11 | 0.11 | 0.13 | 0.11 |
| | 28 days | % Dimer | 0.12 | 0.13 | 0.12 | 0.17 | 0.12 |
| | | % Total Deg. Prod. | 0.12 | 0.13 | 0.12 | 0.17 | 0.12 |
| 60° C./75% RH | 14 days | % Dimer | 0.32 | 0.48 | 0.29 | 0.33 | 0.40 |
| | | % Total Deg. Prod. | 0.55 | 1.0 | 0.48 | 0.54 | 0.52 |
| | 28 days | % Dimer | 0.27 | 0.64 | 0.33 | 0.40 | 0.53 |
| | | % Total Deg. Prod. | 0.47 | 1.4 | 0.58 | 0.85 | 0.53 |
| 70° C./10% RH | 14 days | % Dimer | 0.11 | 0.09 | 0.10 | 0.10 | 0.11 |
| | | % Total Deg. Prod. | 0.11 | 0.09 | 0.10 | 0.10 | 0.11 |
| | 28 days | % Dimer | 0.11 | 0.11 | 0.10 | 0.10 | 0.10 |
| | | % Total Deg. Prod. | 0.11 | 0.11 | 0.10 | 0.10 | 0.10 |
| 70° C./40% RH | 14 days | % Dimer | 0.14 | 0.14 | 0.12 | 0.14 | 0.15 |
| | | % Total Deg. Prod. | 0.14 | 0.14 | 0.12 | 0.14 | 0.15 |
| | 28 days | % Dimer | 0.14 | 0.14 | 0.14 | 0.16 | 0.17 |
| | | % Total Deg. Prod. | 0.14 | 0.14 | 0.14 | 0.16 | 0.17 |
| 70° C./75% RH | 1 day | % Dimer | 0.25 | 0.27 | 0.26 | 0.25 | 0.17 |
| | | % Total Deg. Prod. | 0.25 | 0.27 | 0.26 | 0.25 | 0.17 |
| | 7 days | % Dimer | 0.38 | 0.56 | 0.37 | 0.45 | 0.40 |
| | | % Total Deg. Prod. | 0.63 | 1.2 | 0.63 | 0.80 | 0.54 |
| 80° C./40% RH | 2 days | % Dimer | 0.19 | 0.20 | 0.26 | 0.30 | 0.15 |
| | | % Total Deg. Prod. | 0.19 | 0.20 | 0.34 | 0.40 | 0.15 |

TABLE 7-continued

Degradation Results for Experimental Tablets A, B, C, E, and G Under ASAP Conditions Between 1 and 28 Days

| Conditions | Time | Impurities | A | B | C | E | G |
|---|---|---|---|---|---|---|---|
| | | | Experimental Tablet Formulations | | | | |
| | 7 days | % Dimer | 0.20 | 0.28 | 0.30 | 0.33 | 0.19 |
| | | % Total Deg. Prod. | 0.29 | 0.39 | 0.71 | 0.79 | 0.19 |

Figure 16:
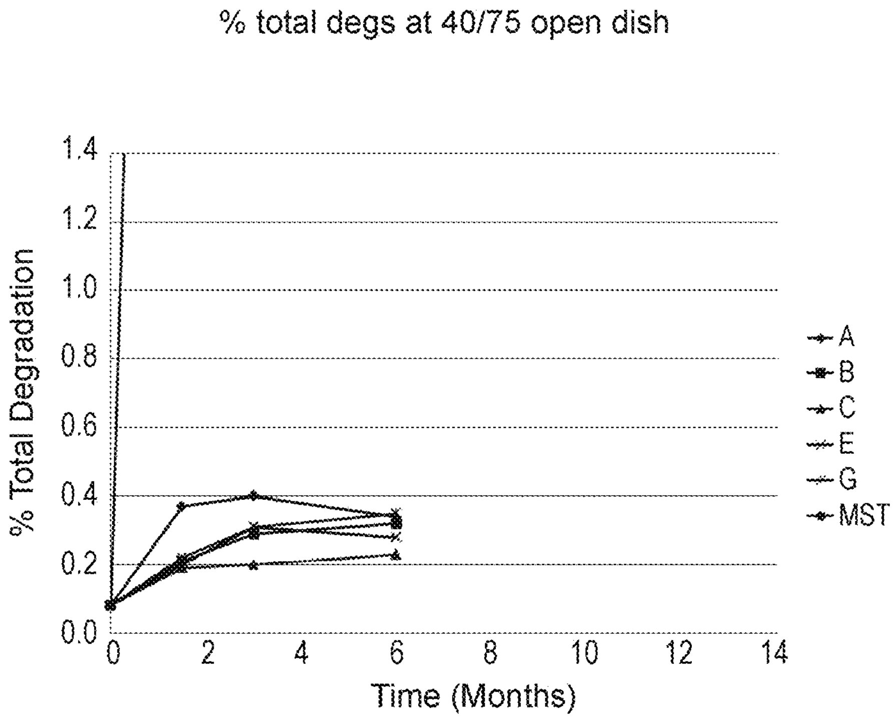
FIG. 16 provides the percentage of total degradation products detected in tablets prepared from the experimental formulations A, B, C, E, and G and in the MST tablets at 40° C./75% RH in an open dish over a six-month period.

FIGS. 12, 13, 14, and 15 provide the level of dimer detected in tablets prepared from experimental formulations A, B, C, E and G and from the MST tablets in an open dish for six months at 500, 25° C./60% RH, 30° C./75% RH, and 40° C./75% RH, respectively. When stored at 500, none of the formulations showed any significant increase in dimer. When stored at 25° C./60% RH, no increase of the dimer was observed for the experimental tablets (A, B, C, E and G) after six months whereas detection of the dimer rose above the acceptable criteria of 0.7% for the MST tablets after six weeks. When stored at 30° C./75% RH, the level of dimer increased for all the batches but remained below 0.7% for the experimental tablets whereas the level of dimer in the MST tablets was far above the acceptance criteria after six weeks. When stored at 40° C./75% RH, the level of dimer followed a similar trend to that at 30° C./75% RH up to three months for lots A, B, C, E and G. Unexpectedly at the six month date, the percentage of dimer detected slightly decreased for lots A, C and E. Further, the total percentage of degradation products detected decreased for lots A and E after six months at 40° C./75% RH (FIG. 16). This decrease in degradation over time may be due to formation of the trimer and/or higher oligomers.

Table 8 provides the numerical comparison of percentages of dimer and total degradation products detected in experimental tablets A, B, C, E, and G and in the MST tablets at six weeks, three months, and six months.

TABLE 8

Percentage of Dimer and Total Degradation Products Detected in Experimental Tablets A, B, C, E, and G and in the MST Tablets at 6 Weeks, 3 Months, and 6 Months

| Conditions | Time | | A | B | C | E | G | MST |
|---|---|---|---|---|---|---|---|---|
| | | | Tablet Formulations | | | | | |
| | Initial | % Dimer | 0.08 | 0.08 | 0.08 | 0.08 | 0.08 | 0.08 |
| | | % Total* | 0.08 | 0.08 | 0.08 | 0.08 | 0.08 | 0.08 |
| 5° C. | 6 weeks | % Dimer | 0.08 | 0.08 | 0.08 | 0.07 | 0.08 | 0.08 |
| | | % Total* | 0.08 | 0.08 | 0.08 | 0.07 | 0.08 | 0.08 |
| | 3 months | % Dimer | 0.08 | 0.08 | 0.08 | 0.08 | 0.07 | 0.09 |
| | | % Total* | 0.08 | 0.08 | 0.08 | 0.08 | 0.07 | 0.09 |
| | 6 months | % Dimer | 0.07 | 0.07 | 0.07 | 0.07 | 0.07 | 0.09 |
| | | % Total* | 0.07 | 0.07 | 0.07 | 0.07 | 0.07 | 0.09 |
| 25° C./60% RH | 6 weeks | % Dimer | 0.08 | 0.09 | 0.08 | 0.10 | 0.09 | 0.73 |
| | | % Total* | 0.08 | 0.09 | 0.08 | 0.10 | 0.09 | 0.83 |
| open dish | 3 months | % Dimer | 0.10 | 0.08 | 0.10 | 0.10 | 0.10 | 1.1 |
| | | % Total* | 0.10 | 0.08 | 0.10 | 0.10 | 0.10 | 1.3 |
| | 6 months | % Dimer | 0.11 | 0.09 | 0.09 | 0.10 | 0.09 | 1.3 |
| | | % Total* | 0.11 | 0.09 | 0.09 | 0.10 | 0.09 | 1.8 |
| 30° C./75% RH | 6 weeks | % Dimer | 0.20 | 0.13 | 0.11 | 0.15 | 0.12 | 2.6 |
| | | % Total* | 0.20 | 0.13 | 0.11 | 0.15 | 0.12 | 4.1 |
| open dish | 3 months | % Dimer | 0.26 | 0.14 | 0.15 | 0.17 | 0.16 | 2.8 |
| | | % Total* | 0.26 | 0.14 | 0.15 | 0.17 | 0.16 | 5.9 |
| | 6 months | % Dimer | 0.26 | 0.16 | 0.15 | 0.17 | 0.18 | — |
| | | % Total* | 0.34 | 0.16 | 0.15 | 0.17 | 0.18 | — |
| 40° C./75% RH | 6 weeks | % Dimer | 0.30 | 0.21 | 0.19 | 0.20 | 0.22 | 3.1 |
| | | % Total* | 0.37 | 0.21 | 0.19 | 0.20 | 0.22 | 7.2 |

TABLE 8-continued

Percentage of Dimer and Total Degradation Products Detected in Experimental Tablets A, B, C, E, and G and in the MST Tablets at 6 Weeks, 3 Months, and 6 Months

| Conditions | Time | | A | B | C | E | G | MST |
|---|---|---|---|---|---|---|---|---|
| | | | Tablet Formulations | | | | | |
| open dish | 3 months | % Dimer | 0.30 | 0.23 | 0.20 | 0.23 | 0.25 | 2.7 |
| | | % Total* | 0.40 | 0.29 | 0.20 | 0.31 | 0.31 | 8.7 |
| | 6 months | % Dimer | 0.24 | 0.23 | 0.17 | 0.20 | 0.26 | — |
| | | % Total* | 0.34 | 0.32 | 0.23 | 0.28 | 0.35 | — |

*% Total means percentage of total degradation products detected.

With regard to appearance (Table 9), no change in color was observed in any of the tablets prepared from experimental formulations A, B, C, E, and G after twenty eight days storage at 5000/75% RH, 6000/40% RH and 7000/10% RH. Similarly, no change was recorded after seven days storage at 7000/75% RH. Yellow mottling was observed for experimental tablets A, B, C, and E after seven days at 8000/40% RH but not for the tablets from lot G (starch and fumaric acid). The tablets from lot A (DCP filler) exhibited discoloration on the sides of the tablets after twenty-eight days at 6000/75% RH. The tablets from lot E (lactose filler) showed signs of mottling after twenty-eight days at 7000/40% RH. The tablets from lot G (starch and fumaric acid) displayed a light yellowing after twenty-eight days at 6000/75% RH. The ASAP appearance results demonstrated that the experimental formulations A, B, C, E, and G had improved behavior with respect to color change when compared to the MST tablets.

TABLE 9

Appearance Results for Experimental Tablet Formulations A, B, C, E, and G Under ASAP Conditions Between 1 and 28 Days

| Exp. Tablet | | A | B | C | E | G |
|---|---|---|---|---|---|---|
| 5° C. control | | White | White | White | White | White |
| 50° C./75% RH | 14 d | blistering | blistering | blistering | blistering | Off-white |
| | 28 d | blistering | blistering | blistering | blistering | Off-white |
| 60° C./40% RH | 14 d | blistering | blistering | blistering | blistering | Off-white |
| | 28 d | blistering | blistering | blistering | blistering | Off-white |
| 60° C./75% RH | 14 d | blistering | blistering | blistering | blistering | Off-white |
| | 28 d | blistering, dark yellow | blistering | blistering | pitting | light yellow |
| 70° C./10% RH | 14 d | blistering | blistering | blistering | blistering | Off-white |
| | 28 d | blistering | blistering | blistering | pitting | Off-white |
| 70° C./40% RH | 14 d | blistering | blistering | blistering | blistering | Off-white |
| | 28 d | blistering | blistering | blistering | blistering, mottling | Off-white |
| 70° C./75% RH | 1 d | blistering | blistering | blistering | pitting | Off-white |
| | 7 d | blistering | blistering | blistering | pitting | Off-white |
| 80° C./40% RH | 2 d | blistering | blistering | blistering | yellow mottling | Off-white |
| | 7 d | blistering, yellow mottling | blistering, yellow mottling | blistering, yellow mottling | yellow mottling | Off-white |

With regard to appearance at 6 weeks, 3 months, and 6 months, yellow and brown spots were observed for the MST tablets at six weeks at 30° C./75% RH and 40° C./75% RH. For the tablets prepared from experimental formulations A, B, C, E, and G, only lot A showed a change in color when stored at 40° C./75% RH for three months (off-white) and six months (pale yellow). The six week, three month, and six month appearance results are provided in Table 10 for the tablets prepared from experimental formulations A, B, C, E, and G and from the MST tablets.

TABLE 10

6 Week, 3 Month, and 6 Month Appearance Results for Experimental Tablets A, B, C, E, and G and for the MST Tablets

| | | Tablet Formulations | | | | | |
|---|---|---|---|---|---|---|---|
| | | A | B | C | E | G | MST |
| Initial | | white to off-white | white to off-white | white to off-white | white to off-white | white to off-white | white to off-white |
| 5° C. | 6 weeks | white to off-white | white to off-white | white to off-white | white to off-white | white to off-white | white to off-white |
| | 3 months | white to off-white | white to off-white | white to off-white | white to off-white | white to off-white | white to off-white |
| | 6 months | white to off-white | white to off-white | white to off-white | white to off-white | white to off-white | white to off-white |
| 25° C. 60% RH | 6 weeks | white to off-white | white to off-white | white to off-white | white to off-white | white to off-white | white to off-white |
| | 3 months | white to off-white | white to off-white | white to off-white | white to off-white | white to off-white | white to off-white |
| | 6 months | white to off-white, blistering | white to off-white, blistering | white to off-white, blistering | white to off-white, blistering | white to off-white, blistering | off-white |
| 30° C. 75% RH | 6 weeks | white to off-white | white to off-white | white to off-white | white to off-white | white to off-white | white to off-white, yellow spots |
| | 3 months | white to off-white | white to off-white | white to off-white | white to off-white | white to off-white | off-white, light brown spots |
| | 6 months | Off-white, blistering | white to off-white, blistering | white to off-white, blistering | white to off-white, with blistering | white to off-white, blistering | N/A |
| 40° C. 75% RH | 6 weeks | white to off-white | white to off-white | white to off-white | white to off-white | white to off-white | white to off-white, brown spots |
| | 3 months | Off-white tablet | white to off-white | white to off-white | white to off-white | white to off-white | Off-white, brown spots |
| | 6 months | Pale yellow, mottling | white to off-white, blistering | white to off-white, blistering | white to off-white, blistering | white to off-white, blistering | N/A |

The results for the experimental formulations A, B, C, E, and G demonstrated that these formulations have an improved stability profile compared to the MST formulation used in the Phase II clinical studies. The six-month stability profiles showed that the formation of the dimer product in the experimental formulations remained below 0.7% under all of the conditions investigated including 40° C. and 75% relative humidity. In terms of appearance only the tablets containing di-calcium phosphate (DCP) exhibited any change in color likely due to DCP acting as a proton acceptor albeit a relatively weak one compared to the proton acceptor excipients excluded from this study.

Although the experimental formulations showed improved stability, further studies were warranted as each formulation had advantages and shortcomings with respect to the production of an immediate release tablet. The use of DCP was deemed not favored due to the discoloration observed over the six-month storage period. Mannitol, while potentially generating the most stable blend, exhibited the greatest observable challenge with respect to handling, processing and punch adhesion. Starch containing blends were easier to process but there were concerns around batch to batch variability of this particular excipient. Lactose appeared to be relatively easy to process and was considered an alternative to DCP based tablet formulations, however, there were concerns regarding the use of this excipient with lactose intolerant subjects. From a tablet formulation only perspective, the preferred order was determined to be lactose, starch, and mannitol.

With regard to the use of lubricants or flow agents, glyceryl dibehenate reduced the ejection force compared to samples containing silicon dioxide which supported the use of glyceryl dibehenate as a suitable lubricating agent. However, bulk flow observations suggested that glyceryl dibehenate detrimentally impacted tablet hardness and punch adhesion. Further studies were clearly warranted to study the effect of formulation composition (e.g. filler ratio) and potentially the addition of small levels of silicon dioxide (≤0.5%) as a flow agent.

The addition of the disintigrant crospovidone to the formulation did not appear to impact disintegration, dissolution, nor the stability of the product. Nonetheless, the optimum amount of disintegrant included in the formulation required further studies.

Fumaric acid was investigated to determine whether the inclusion of a non-hygroscopic acidifying agent enhanced the stability of the drug product. Results appeared to demonstrate that the addition of this material had no impact on the stability of the experimental tablets. Whether tablet stabilization was due to the addition of fumaric acid or the absence of proton acceptor excipients required further experiments.

While stability results for the experimental formulations supported the realization that an immediate release tablet drug product was feasible for PF-06651600-15, several areas still needed to be investigated to advance a formulation from a concept to clinical and commercial product. In particular, further development was required to develop an optimized formulation and a robust manufacturing process. Studies examined direct compression only and these limited observations indicated that the current blends had issues with respect to both flow and punch adhesion. Lubricant and disintegrant levels, filler ratios and PF-06651600-15 content all required further investigation. In addition, blending, roller compaction and compression conditions needed to be explored to understand the impact of product processing upon the formulation.

Furthermore, film coating studies were required to demonstrate whether this additional step would negatively impact the stability of the PF-06651600-15 tablet. Previous results demonstrated that an aqueous coating of the MST tablet induced degradation of PF-06651600-15. Additional experiments using a stable tablet formulation with both an aqueous and a solvent coat were required to determine whether a film coated tablet was a viable option with regard to PF-06651600-15 product development. If film coating studies induced instability of PF-06651600-15, then father studies using lactose, starch and mannitol formulations would be warranted to determine whether an encapsulated product would be stable.

In sum, the experimental formulations for PF-06651600-15 demonstrated that, with compatible excipients, an improved immediate release tablet compared to the MST tablet appeared to be possible. However, further research was required to determine whether these formulations were stable beyond six months and whether the formulations were amendable to further manufacture processing including powder flow, dry granulation/roller compaction, tablet film coating, and encapsulation.

Figure 17:
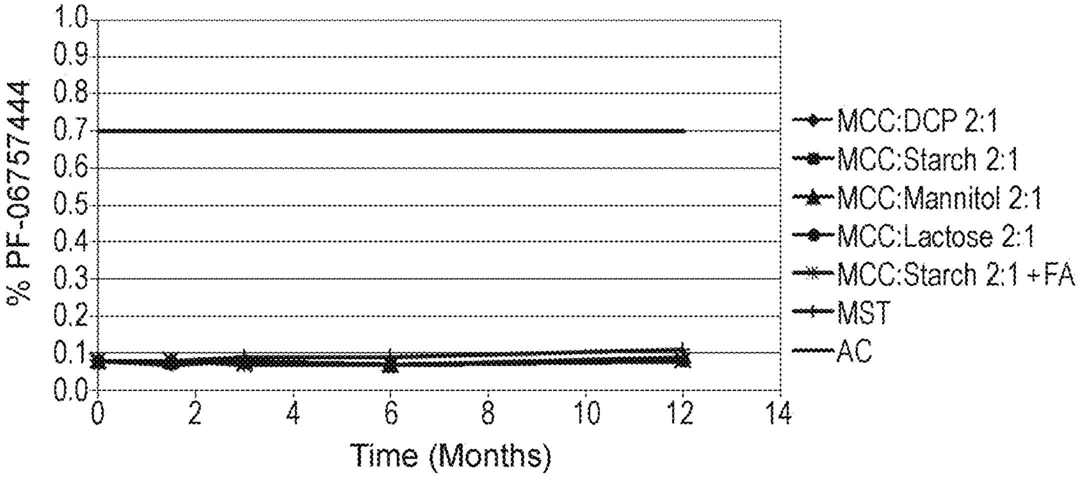
FIG. 17 provides the percentage of dimer detected in tablets prepared from the experimental formulations A, B, C, E and G and in the MST tablets at 5° C. at twelve months. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation. AC means acceptance criteria which is 0.7%.
Figure 18:
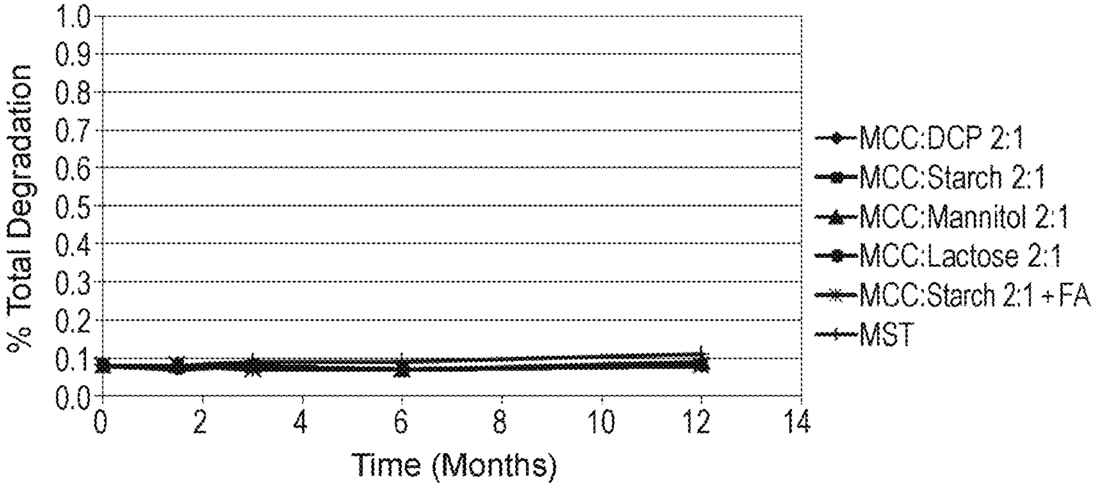
FIG. 18 provides the percentage of total degradation products detected in tablets prepared from the experimental formulations A, B, C, E and G and in the MST tablets at 5° C. at twelve months. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation.
Figure 19:
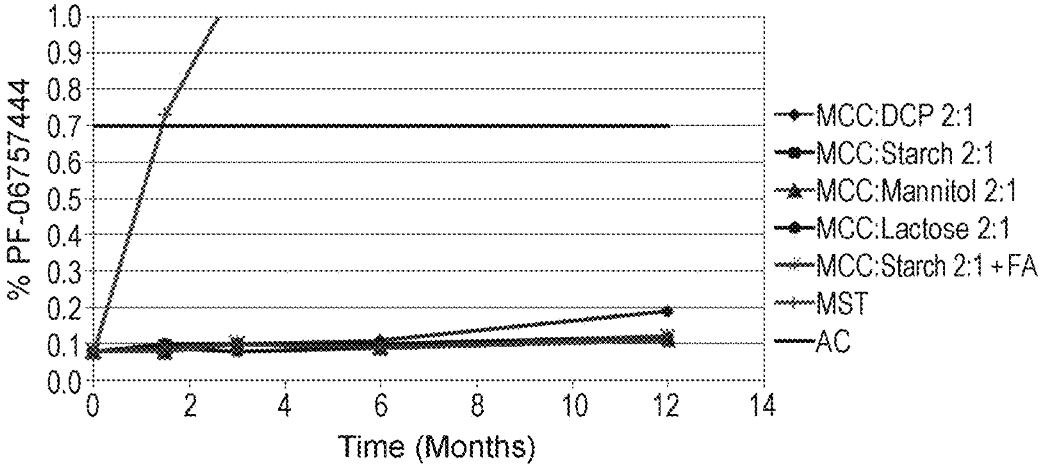
FIG. 19 provides the percentage of dimer detected in tablets prepared from the experimental formulations A, B, C, E and G and in the MST tablets at 25° C./60% RH in an open dish over a twelve-month period. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation. AC means acceptance criteria which is 0.7%.
Figure 20:
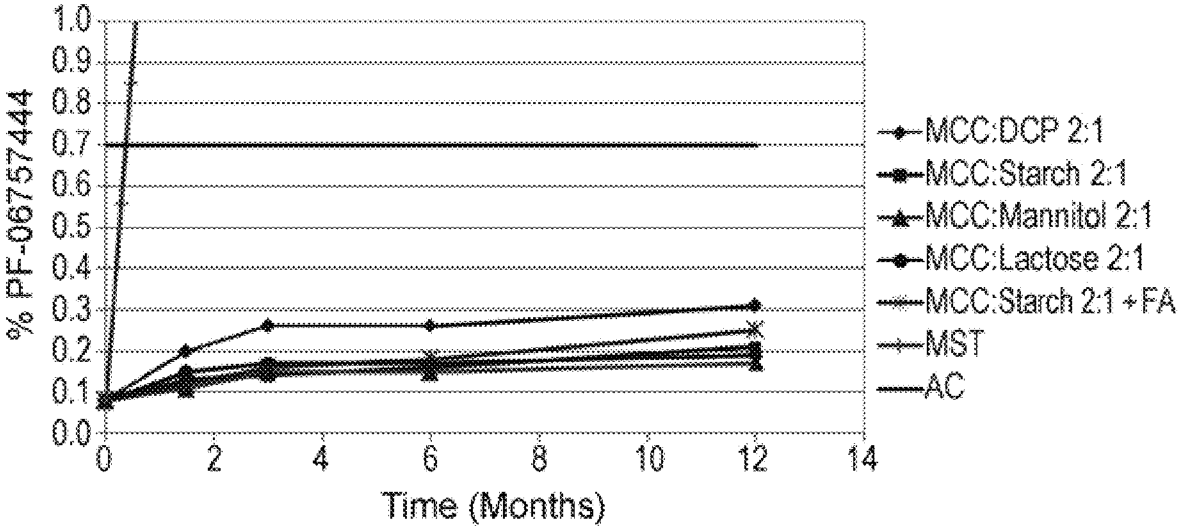
FIG. 20 provides the percentage of dimer detected in tablets prepared from the experimental formulations A, B, C, E and G and in the MST tablets at 30° C./75% RH in an open dish over a twelve-month period. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation. AC means acceptance criteria which is 0.7%.
Figure 21:
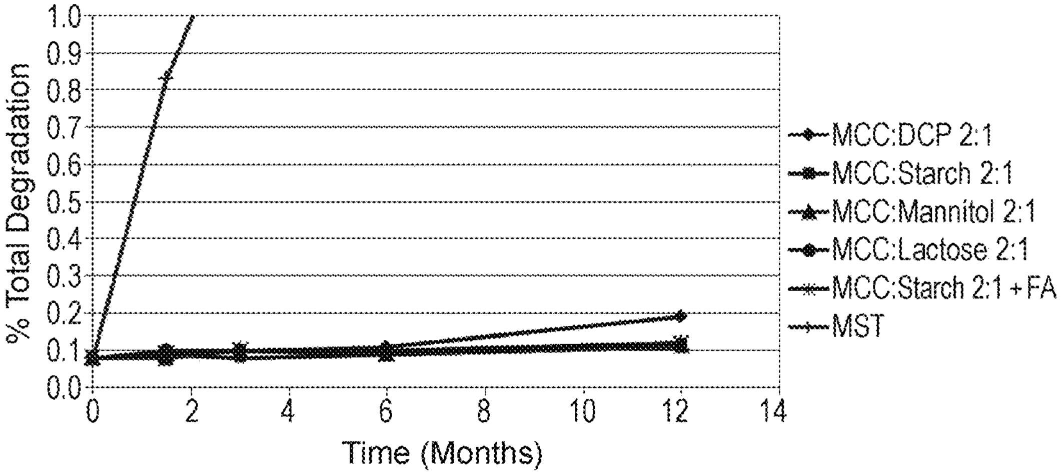
FIG. 21 provides the percentage of total degradation products detected in tablets prepared from the experimental formulations A, B, C, E and G and in the MST tablets at 25° C./60% RH in an open dish over a twelve-month period. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation.
Figure 22:
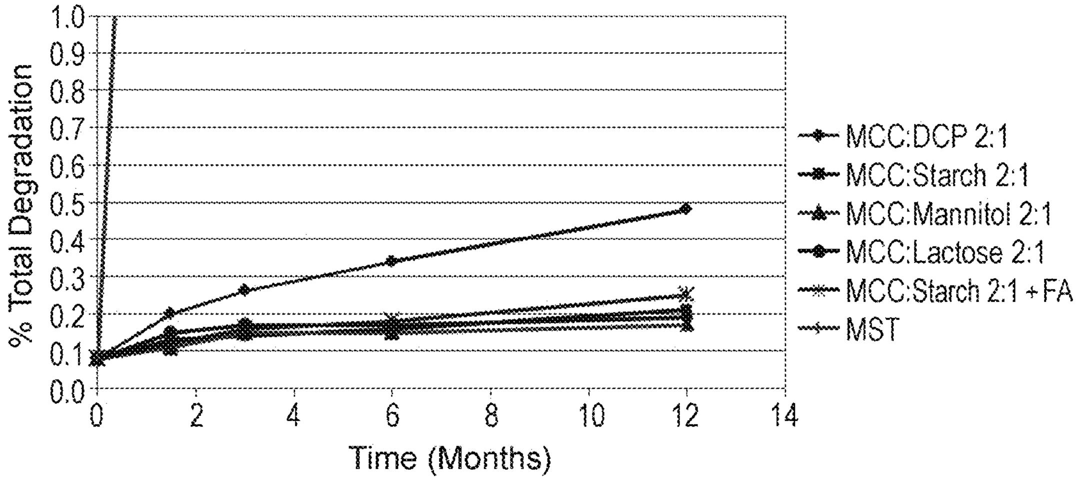
FIG. 22 provides the percentage of total degradation products detected in tablets prepared from the experimental formulations A, B, C, E and G and in the MST tablets at 30° C./75% RH in an open dish over a twelve-month period. MCC:DCP 2:1 means experimental formulation A. MCC:Starch 2:1 means experimental formulation B. MCC:Mannitol 2:1 means experimental formulation C. MCC:Lactose 2:1 means experimental formulation E. MCC:Starch+FA means experimental formulation G. MST means the MST formulation.

A twelve month stability study was conducted for the 50 mg tablets prepared from the experimental formulations A, B, C, E, and G compared to the 50 mg tablet prepared from the MST formulation under the following conditions 5° C., 25° C./60% RH, and 30° C./75% in an open dish. All the tablets remained below the acceptance criteria of 0.7% for detection of dimer and total degradation products at 5° C. for twelve months (FIGS. 17 and 18). With regard to dimer formation, the study results showed that all of the experimental tablets remained below the acceptance criteria of 0.7% after twelve months in an open dish under the conditions of 25° C./60% RH (FIG. 19) and 30° C./75% (FIG. 20). The experimental tablets exhibited similar profiles with regard to dimer production while the tablets derived from formulation A, containing DCP, produced the highest amounts of dimer under both conditions. The MST tablets exceeded the acceptance criteria of 0.7% for dimer detection within two months under both conditions. With regard to the percentage of total degradation products detected, again, all the experimental tablets remained below the acceptance criteria of 0.7% over the twelve month period in an open dish under the conditions of 25° C./60% RH (FIG. 21) and 30° C./75% (FIG. 22). Further, experimental tablets B, C, E, and G exhibited similar total degradation product profiles while the tablets from formulation A demonstrated a linear upward trend under both conditions reaching 0.48% under the 30° C./75% RH conditions at twelve months (Table 11). The MST tablets exceeded the acceptance criteria of 0.7% total degradation products detected within 2 months for both conditions.

TABLE 11

Percentages of Dimer and Total Degradation Products Detected for Experimental Tablets A, B, C, E, and G and for the MST Tablets After 12 Months

| | Lots | | | | | |
|---|---|---|---|---|---|---|
| Conditions | A | B | C | E | G | MST |
| 5° C. (%) Dimer | 0.08 | 0.08 | 0.09 | 0.08 | 0.08 | 0.11 |
| 5° C. (%) Total Degradation Products | 0.08 | 0.08 | 0.09 | 0.08 | 0.08 | 0.11 |
| 25° C./60% RH (%) Dimer | 0.19 | 0.11 | 0.11 | 0.12 | 0.12 | 2.4 |
| 25° C./60% RH (%) Total Degradation Products | 0.19 | 0.11 | 0.11 | 0.12 | 0.12 | 4.2 |
| 30° C./750% RH (%) Dimer | 0.31 | 0.21 | 0.17 | 0.19 | 0.25 | — |
| 30° C./750% RH (%) Total Degradation Products | 0.48 | 0.21 | 0.17 | 0.19 | 0.25 | — |

The degradation results disclosed herein for the experimental tablets demonstrated that tablets derived from formulation C (Table 2) had produced the lowest amount of degradation products under most of the conditions studied at three months (Table 8), six months (Table 8), twelve months (Table 11), and under ASAP conditions (Table 7 and FIG. 11). However, the manufacturing characteristics with regard to flow and punch adhesion were poor for blend C (Table 3).

Studies were therefore conducted on the stability of experimental formulation C encapsulated in hydroxypropyl methylcellulose (HPMC) capsules compared to tablet and powder blend, where the powder blend was not compacted into a tablet nor encapsulated. The purpose was to evaluate whether PF-06651600-15 compatibility could be achieved between a powder blend and a HPMC capsule shell in order to mitigate any tablet production issues that may arise due to poor powder blend processing characteristics. The stability of PF-06651600-after HPMC encapsulation was not predictable, in part, because of the potential detrimental effect formaldehyde and/or formic, leached from the capsules, might have on product stability.

HPMC capsules (Vcaps Plus, size 0, white/opaque) were each filled with 250 mgs of experimental formulation C (25 mg API dose) which was the maximum amount of blend that could be contained within this capsules size. Chemical stability was assessed under ASAP conditions after the capsules were opened and the bottom half containing blend was positioned upright in a glass vial to allow the blend to equilibrate with the environmental conditions while maintaining contact with the capsule shell. The harsher ASAP conditions, 70° C./75% RH and 80° C./40%, were not assessed in this study due to the properties of the HPMC shell.

With regard to appearance of the encapsulated experimental blend C, no bulk or localized color changes were observable in any of the samples.

Figure 23A:
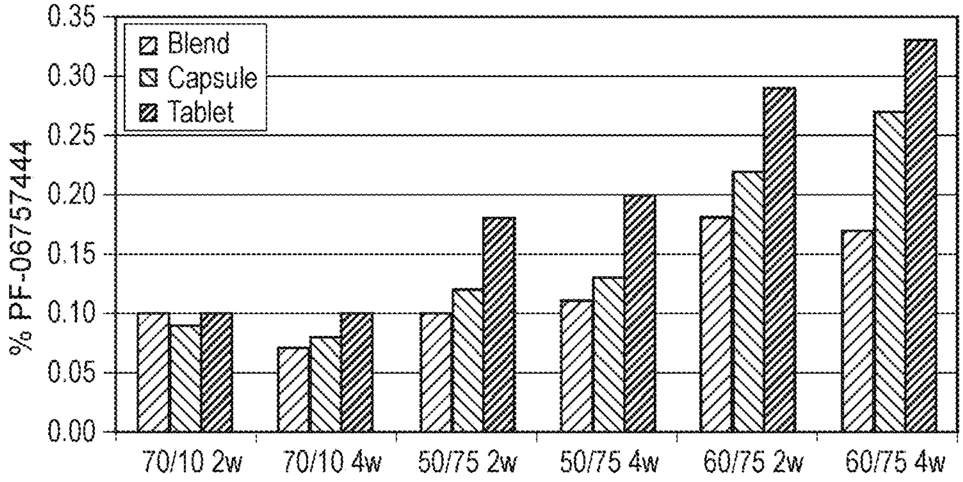
FIG. 23 provides the percentage of dimer (top panel) and total degradation products (bottom) detected for experimental formulation C under certain ASAP conditions while: inside hydroxypropyl methylcellulose (HPMC) capsules; alone; and compacted (tablet). The 50° C./75% RH condition was actually 50° C./68% RH. The order from left to right for each condition is blend alone, blend HPMC encapsulated, and blend compacted as a tablet.
Figure 23B:
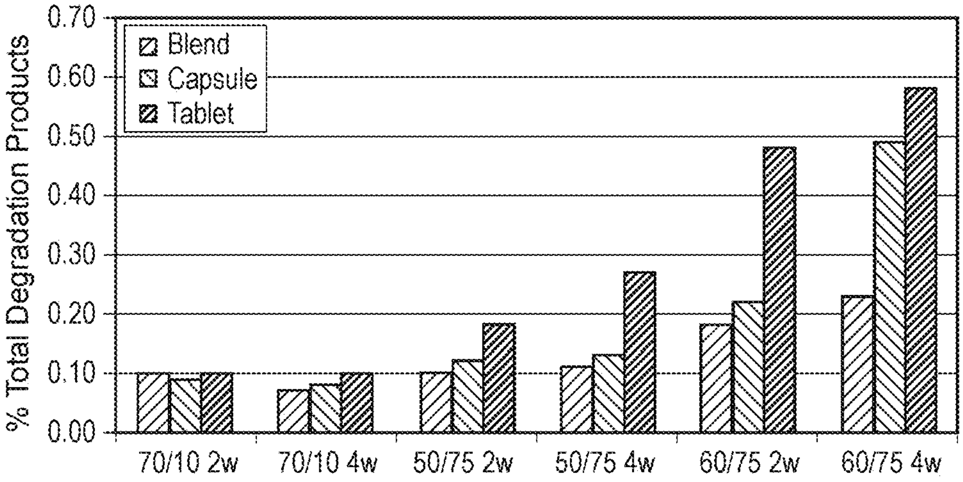

The dimer and total degradation product results (Table 12) demonstrated that a 10% w/w active blend containing mannitol and microcrystalline cellulose in a ratio of 2:1 and 2% glyceryl dibehenate exhibited acceptable compatibility with a size 0, HPMC capsule. The encapsulated product displayed an improved accelerated stability profile when compared to an equivalent tablet but was less stable than the blend alone (FIG. 23 and Tables 13 and 14).

TABLE 12

Percentage of Dimer and Total Degradation Products Detected for Experimental Blend C Encapsulated in HPMC Capsules Under ASAP Conditions

| Stability Condition | Time | Dimer (%) | Total Degradation Products (%) |
|---|---|---|---|
| 5° C. | | 0.09 | 0.09 |
| 40° C./75% RH | 6 weeks | 0.10 | — |
| | 8 weeks | 0.11 | — |
| 50° C./30% RH | 2 weeks | 0.09 | 0.09 |
| | 4 weeks | 0.09 | 0.09 |
| 50° C./68% RH | 2 weeks | 0.12 | 0.12 |
| | 4 weeks | 0.13 | 0.13 |
| 60° C./10% RH | 2 weeks | 0.09 | 0.09 |
| | 4 weeks | 0.10 | 0.10 |
| 60° C./30% RH | 2 weeks | 0.09 | 0.09 |
| | 4 weeks | 0.09 | 0.09 |
| 60° C./65% RH | 2 weeks | 0.13 | 0.13 |
| | 4 weeks | 0.14 | 0.14 |
| 60° C./75% RH | 2 weeks | 0.22 | 0.22 |
| | 4 weeks | 0.27 | 0.49 |
| 70° C./10% RH | 2 weeks | 0.09 | 0.09 |
| | 4 weeks | 0.08 | 0.08 |

TABLE 13

Percentage of Dimer Detected in Experimental Blend C: Alone; HPMC Encapsulated; and Compacted (Tablet)

| Stability Condition | Time | Blend | Capsule | Tablet |
|---|---|---|---|---|
| 70° C./10% RH | 2 weeks | 0.10 | 0.09 | 0.10 |
| | 4 weeks | 0.07 | 0.08 | 0.10 |
| 50° C./68% RH | 2 weeks | 0.10 | 0.12 | 0.18 |
| | 4 weeks | 0.11 | 0.13 | 0.20 |
| 60° C./75% RH | 2 weeks | 0.18 | 0.22 | 0.29 |
| | 4 weeks | 0.17 | 0.27 | 0.33 |

TABLE 14

Percentage of Total Degradation Products Detected in Experimental Blend C: Alone; HPMC Encapsulated; and Compacted (Tablet)

| Stability Condition | Time | Blend | Capsule | Tablet |
|---|---|---|---|---|
| 70° C./10% RH | 2 weeks | 0.10 | 0.09 | 0.10 |
| | 4 weeks | 0.07 | 0.08 | 0.10 |
| 50° C./68% RH | 2 weeks | 0.10 | 0.12 | 0.18 |
| | 4 weeks | 0.11 | 0.13 | 0.27 |
| 60° C./75% RH | 2 weeks | 0.18 | 0.22 | 0.48 |
| | 4 weeks | 0.23 | 0.49 | 0.58 |

With regard to formaldehyde and formic acid as potential impurities leached from HPMC capsules, degradation experiments were conducted with PF-06651600-15 in the presence of each impurity separately. For formaldehyde after 3 days at 40° C., a main degradation product was formed at a level of about 80%. The mass spectrometry analysis of the product was consistent with the addition of —CH2O to PF-06651600-15. After 3 days at 40° C. in presence of formic acid, the level of total degradation products reached 24%. The degradation products generated with formaldehyde and formic acid were not detected during analysis of the capsules samples stored under ASAP conditions.

The HPMC capsule degradation results suggested that an encapsulated PF-06651600-drug product was acceptable. However, experimental formulation C only achieved a fill weight of 250 mg or 40 mgs of PF-06651600-15 (25 mgs active) in the size 0 capsule. In comparison, the higher dose MST tablets used in previous clinical studies contained just over 80 mgs of PF-06651600-15 (50 mgs API). Further studies were therefore required to assess whether increased drug loading was possible in a suitably sized capsule to attain higher API doses or whether optimization of the blend ratios could enhance flow and bulk density to allow commercial production of a HPMC capsule containing 50 mgs of API.

Figure 24A:
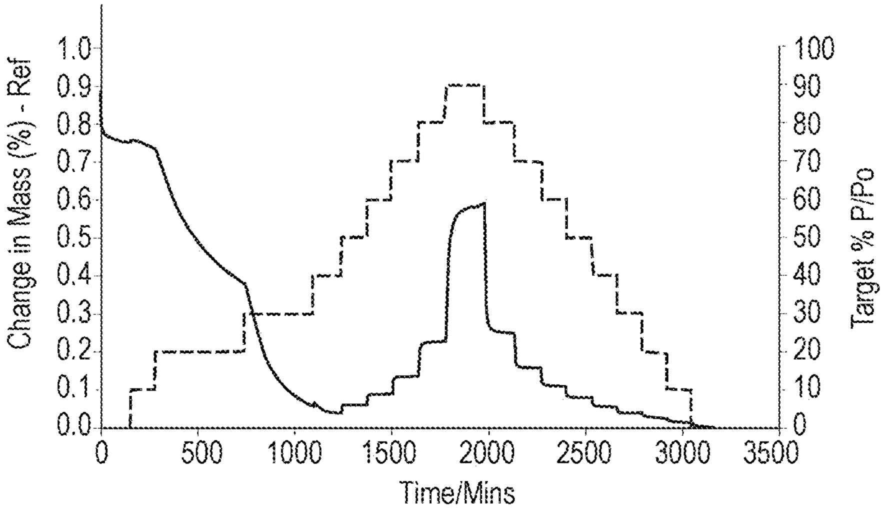
FIG. 24 provides dynamic vapor sorption (DVS) traces for lactose monohydrate (Fast Flo-316; top) and lactose anhydrous (bottom).
Figure 24B:
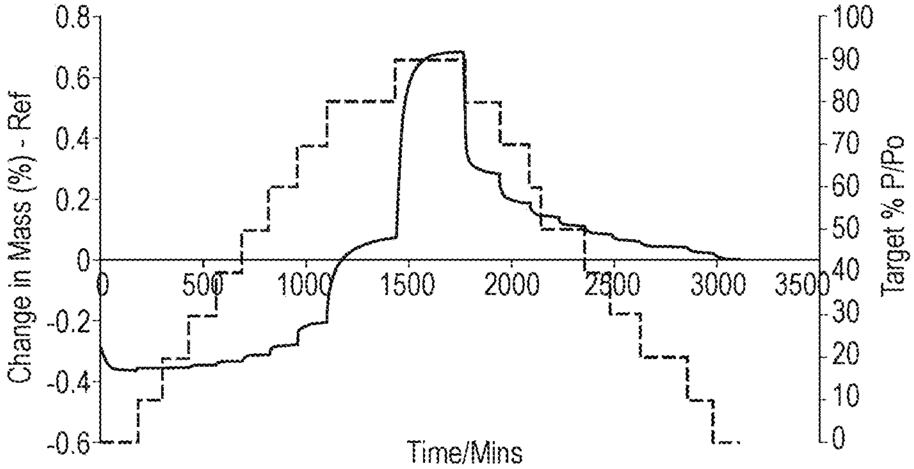

A review of manufacturing properties for filler excipients showed that lactose anhydrous had similar properties as mannitol except that lactose had better flow properties (Table 3). Also noted were the stability results for experimental formulation E, blended with lactose anhydrous. Blend E was slightly less stable than the mannitol containing blend C, however, blend E was below the acceptable limit of 0.7% dimer formation for most of the conditions tested (Tables 7 and 8). Lactose anhydrous was used in blend E rather than lactose monohydrate due to concerns regarding the impact of water upon the degradation of PF-06651600-15. To further explore the hygroscopic properties of lactose monohydrate, dynamic vapor sorption (DVS) traces were generated for both lactose anhydrous and lactose monohydrate (FIG. 24). The results for both were similar as the mass increased less than 2% at a humidity of 90% RH. Lactose monohydrate increased ~0.55% and lactose anhydrous increased ~1.1%. The DVS results indicated that either lactose anhydrous or lactose monohydrate may be acceptable filler excipients in a PF-06651600-15 formulation.

Due to the processing and stability concerns in generating an immediate release tablet, an encapsulated formulation was proposed as a route to commercial drug product development with a target capsule dose range or 10-100 mgs. Blend C was used in the HPMC encapsulated studies and had poor flow properties leading to low capsule fill rates and hence low dosages of active drug. Therefore, studies were initiated with four new experimental formulations, H, I, J, and K containing: lactose monohydrate as the second filler; higher amounts of PF-06651600-15; and different particle sizes to determine the effect of drug loading and API particle size on the physical characteristics of formulations H, I, J, and K (Tables 15 and 16).

TABLE 15

Experimental Blends H, I, J, and K Details

| Blends | Blend Strength (% w/w Active) | Total PF-06651600-15 Concentration (% w/w) | API Particle Size |
|---|---|---|---|
| H | 15 | 24.71% | Un-Milled |
| I | 40 | 65.90% | Un-Milled |
| J | 15 | 24.71% | Milled |
| K | 40 | 65.90% | Milled |

TABLE 16

Experimental Blends H, I, J, and K Compositions

| Component | Experimental Blends H | I | J | K |
|---|---|---|---|---|
| PF-06651600-15 | 114.91 g | 306.43 g | 113.67 g | 303.13 g |
| Microcrystalline Cellulose | 156.45 g | 60.69 g | 154.77 g | 60.04 g |
| Lactose Monohydrate | 156.45 g | 60.69 g | 154.77 g | 60.04 g |

TABLE 16-continued

Experimental Blends H, I, J, and K Compositions

| Component | Experimental Blends H | I | J | K |
|---|---|---|---|---|
| Crospovidone | 13.95 g | 13.95 g | 13.80 g | 13.80 g |
| Glyceryl Dibehenate | 23.25 g | 23.25 g | 23.00 g | 23.00 g |
| Total | 465.01 g | 465.01 g | 460.01 g | 460.01 g |
| PF-06651600-15 | 24.7%* | 65.9%‡ | 24.7%* | 65.9%‡ |
| Microcrystalline Cellulose | 33.6% | 13.0% | 33.6% | 13.0% |
| Lactose Monohydrate | 33.6% | 13.0% | 33.6% | 13.0% |
| Crospovidone | 3.0% | 3.0% | 3.0% | 3.0% |
| Glyceryl Dibehenate | 5.0% | 5.0% | 5.0% | 5.0% |

*15.3% active pharmaceutical agent (API), i.e. PF-06651600

‡40.9% active pharmaceutical agent (API), i.e. PF-06651600

Experimental blends H, I, J, and K were prepared using a blend, screen blend method. Microcrystalline cellulose, PF-06651600-15, lactose monohydrate, crospovidone and glyceryl dibehenate were added to a suitable blending container and blended for 10 minutes at ~46 rpm. The blend was screened through a co-mil fitted with an 813 micron screen and then blended for 10 minutes at ~46 rpm.

A Dott Bonpace InCap capsule filling machine was used to assess the suitability of the four blends for filling into size 0 capsule shells. The filling parameters used are described in Table 17. Fill weights were calculated to produce a 50 mg capsule using the 15% blends and a 100 mg capsule from the 40% blends.

TABLE 17

Capsule Filling Parameters for Experimental Blends H, I, J, and K

| Blend | Blend Type | Disc Thickness | Filling Speed | Capsule Shell Type | Fill Weight (mg) |
|---|---|---|---|---|---|
| H | 15% Un-milled API | 16.5 mm | 1500 caps/hr | HPMC* | 310 |
| I | 40% Un-milled API | 11.0 mm | 1500 caps/hr | HPMC* | 250 |
| J | 15% Milled API | 16.5 mm | 1500 caps/hr | Gelatin‡ | 333 |
| K | 40% Milled API | 11.0 mm | 1500 caps/hr | HPMC* | 250 |

*Size 0 HPMC capsules (VcapsPlus).

‡Size 0 Gelatin capsules.

Particle size distribution for experimental blends H, I, J, and K was determined using laser diffraction and the results are listed in Table 18.

TABLE 18

Particle Size Results for Experimental Blends H, I, J, and K

| Blends | API Conc. (% w/w Active) | API Particle Size (microns) ($D_{[v, 0.9]}$) | Mean Blend Particle Size (microns) $D_{[v, 0.1]}$ | $D_{[v, 0.5]}$ | $D_{[v, 0.9]}$ |
|---|---|---|---|---|---|
| H | 15 | 300.50 | 48.88 | 147.23 | 271.66 |
| I | 40 | 300.50 | 68.67 | 189.68 | 298.17 |
| J | 15 | 120.85 | 20.36 | 104.52 | 230.97 |
| K | 40 | 120.85 | 7.21 | 60.20 | 199.94 |

Blend flow values were measured by shear forces (flow function co-efficient), powder compressibility (Carr's Index), and the powder's ability to fall freely through a hole in a disk (flowdex). The measured flow values listed in Table 19 demonstrated that the larger particle size distributions (i.e. greater $D_{[v,0.1]}$, $D_{[v,0.5]}$ and $D_{[v,0.9]}$ values) had better measured flow values. Unmilled Blends H and I had the largest particles and excellent measured flow values. The milled blends, J and K, had the smallest particles with acceptable to good measured flow values.

TABLE 19

Comparison of Measured Flow Values for Experimental Blends H, I, J, and K

| Blends | API Concentration (% w/w Active) | API ($D_{[v, 0.9]}$) | Blend ($D_{[v, 0.9]}$) | Flow Measurements FFC | Carr's (%) | Flowdex (mm) |
|---|---|---|---|---|---|---|
| H | 15 | 300.50 | 271.66 | 17.2 | 16.15 | 14 |
| I | 40 | 300.50 | 298.17 | 18.0 | 15.52 | 7 |
| J | 15 | 120.85 | 230.97 | 10.4 | 23.64 | 20 |
| K | 40 | 120.85 | 199.94 | 5.5 | 24.57 | 28 |

With regard to stability, all the experimental blends H, I, J, and K showed good stability over a twelve-month period at 30° C./65% RH with respect to appearance (Table 20). All remained white to off-white powders, none were deliquescent. The capsule powder was observed to be loosely compacted and the powder plug was easily broken with little force.

TABLE 20

Experimental Blends H, I, J, and K Stability Appearance Over 12 Months

| Blends | Conditions | 4 Weeks | 8 Weeks | 6 Months | 12 Months |
|---|---|---|---|---|---|
| Blend H | 5° C. | White | White | — | — |
| Un-Milled API | 30° C./65% RH | White | White | White/ Off-White | White/ Off-White |
| 15% w/w | 60° C./40% RH | Off-White/ Pale Yellow | Off-White/ Pale Yellow | — | — |
| Blend I | 5° C. | White | White | — | — |
| Un-Milled API | 30° C./65% RH | White | White | White/ Off-White | White/ Off-White |
| 40% w/w | 60° C./40% RH | Off-White | Off-White | — | — |
| Blend J | 5° C. | White | White | — | — |
| Milled API | 30° C./65% RH | White | White | White/ Off-White | White/ Off-White |
| 15% w/w | 60° C./40% RH | Off-White/ Pale Yellow | Off-White/ Pale Yellow | — | — |

TABLE 20-continued

| Experimental Blends H, I, J, and K Stability Appearance Over 12 Months | | | | | |
|---|---|---|---|---|---|
| Blends | Conditions | 4 Weeks | 8 Weeks | 6 Months | 12 Months |
| Blend K | 5° C. | White | White | — | — |
| Milled API | 30° C./65% RH | White | White | White/ Off-White | White/ Off-White |
| 40% w/w A | 60° C./40% RH | Off-White | Off-White | — | — |

Figure 25:
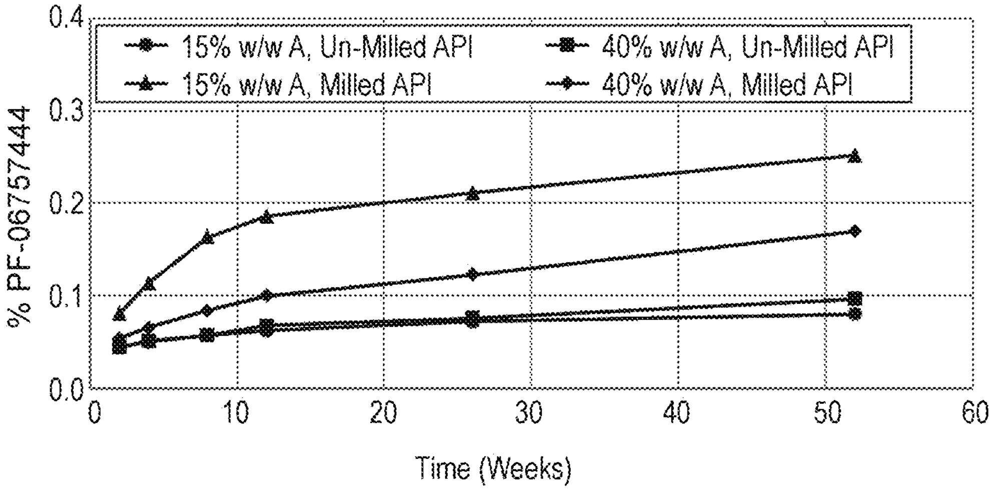
FIG. 25 provides the percentage of dimer detected in the experimental formulations H, I, J, and K at 30° C./65% RH over a twelve-month period. Blend H was unmilled 15% w/w API represented by the circle-shaped points. Blend I was unmilled 40% w/w API represented by the square-shaped points. Blend J was milled 15% w/w API represented by the triangular-shaped points. Blend K was milled 40% w/w API represented by the diamond-shaped points.

FIG. 25 provides the dimer concentration detected in experimental blends H, I, J, and K when stored at 30° C. and 65% relative humidity over a twelve-month period. All the encapsulated blends maintained a level of dimer content below the maximum acceptable limit of 0.7%. The milled blends, J and K, generated higher concentrations of dimer than the unmilled blends, H and I, suggesting that particle size played a role in the amount of dimer produced in these blends. In particular, blend I, unmilled 40% API, was more stable than blend K, milled 40% API.

Table 21 provides the percentages of dimer and total degradant products detected at eight weeks under ASAP conditions for experimental blends H, I, J, and K. The data aligned with the results obtained over one year at 30° C./65% RH (FIG. 25). Lower levels of degradant product formation were observed when a larger API particle size was used within the formulation, blends H and I. In contrast, the smaller particle size used in blends J and K generated higher amounts of degradant. In particular, blend J, containing the milled smaller particle size and the lower product load, 15% w/w PF-06651600-15, in a gelatin capsule was the least stable blend.

TABLE 21

Degradation Results for Experimental Blends H, I, J, and K Under ASAP Conditions at 8 Weeks

| | | | Experimental Blends | | | |
|---|---|---|---|---|---|---|
| Conditions | Time | Impurities | H | I | J | K |
| 5° C. | | % Dimer | 0.04 | 0.04 | 0.05 | 0.04 |
| | | % Total Deg. Prod. | 0.08 | 0.08 | 0.09 | 0.09 |
| 30° C./65% RH | 8 weeks | % Dimer | 0.06 | 0.06 | 0.16 | 0.08 |
| | | % Total Deg. Prod. | 0.09 | 0.10 | 0.32 | 0.13 |
| 40° C./30% RH | 8 weeks | % Dimer | 0.05 | 0.05 | 0.13 | 0.07 |
| | | % Total Deg. Prod. | 0.09 | 0.11 | 0.27 | 0.13 |
| 40° C./50% RH | 8 weeks | % Dimer | 0.05 | 0.05 | 0.13 | 0.07 |
| | | % Total Deg. Prod. | 0.09 | 0.12 | 0.28 | 0.13 |
| 50° C./30% RH | 8 weeks | % Dimer | 0.06 | 0.07 | 0.16 | 0.09 |
| | | % Total Deg. Prod. | 0.13 | 0.14 | 0.34 | 0.18 |
| 50° C./50% RH | 8 weeks | % Dimer | 0.05 | 0.06 | 0.15 | 0.08 |
| | | % Total Deg. Prod. | 0.12 | 0.13 | 0.33 | 0.15 |
| 60° C./40% RH | 8 weeks | % Dimer | 0.06 | 0.06 | 0.18 | 0.09 |
| | | % Total Deg. Prod. | 0.13 | 0.13 | 0.39 | 0.16 |
| 60° C./10% RH | 8 weeks | % Dimer | 0.04 | 0.04 | 0.11 | 0.06 |
| | | % Total Deg. Prod. | 0.09 | 0.11 | 0.13 | 0.12 |

Figure 26:
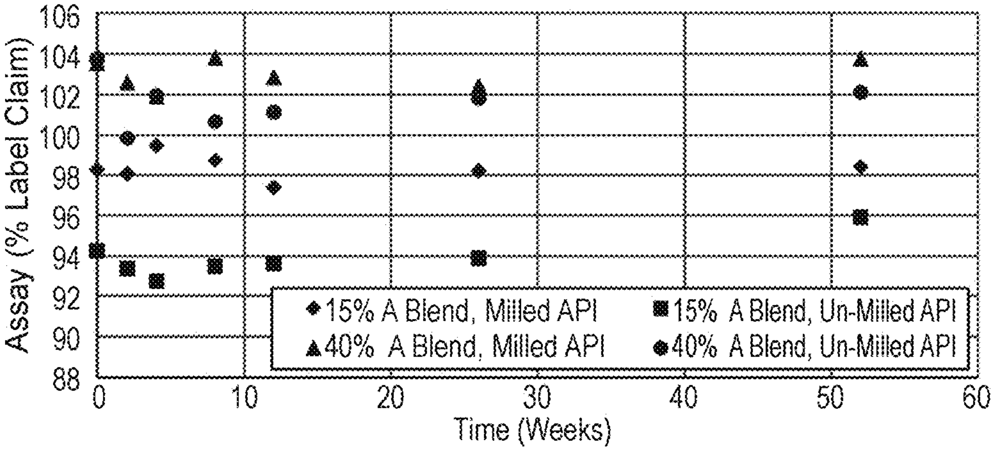
FIG. 26 provides mean assay values for experimental blends H, I, J, and K in capsules at 30°/65% RH over twelve months. Blend H was unmilled 15% w/w API represented by the square-shaped points. Blend I was unmilled 40% w/w API represented by the circle-shaped points. Blend J was milled 15% w/w API represented by the diamond-shaped points. Blend K was milled 40% w/w API represented by the triangular-shaped points.

FIG. 26 provides the mean assay values (% label claim) for experimental blends H, I, J, and K when stored at 30° C. and 65% relative humidity over a twelve-month period. Despite some minor variation over this period, all four blends maintained content similar to that recorded at the initial timepoint (within ±2%). There was no reduction in the assay amounts recorded for any blend during the twelve-month period.

Table 22 provides the numerical values (% label claim) generated for blends H, I, J, and K under ASAP conditions.

TABLE 22

ASAP Results for Experimental Encapsulated Formulations H, I, J, and K

| | | Experimental Blends | | | |
|---|---|---|---|---|---|
| Conditions | Time | H | I | J | K |
| 30° C./65% RH | 0 weeks | 94.2 | 103.8 | 98.3 | 103.5 |
| | 2 weeks | 93.4 | 99.8 | 98.1 | 102.6 |
| | 4 weeks | 92.7 | 102.0 | 99.5 | 101.9 |
| | 8 weeks | 93.5 | 100.6 | 98.7 | 103.8 |
| | 12 weeks | 93.6 | 101.1 | 97.4 | 102.8 |
| | 26 weeks | 93.9 | 101.8 | 98.2 | 102.4 |
| | 52 weeks | 95.9 | 102.1 | 98.4 | 103.7 |
| 40° C./30% RH | 0 weeks | 94.2 | 103.8 | 98.3 | 103.5 |
| | 2 weeks | 92.4 | 98.7 | 94.9 | 101.0 |
| | 4 weeks | 94.0 | 100.1 | 98.8 | 104.3 |
| | 8 weeks | 101.0 | 104.6 | 99.1 | 103.7 |
| 40° C./50% RH | 0 weeks | 94.2 | 103.8 | 98.3 | 103.5 |
| | 2 weeks | 93.1 | 99.9 | 96.9 | 102.9 |
| | 4 weeks | 94.3 | 103.4 | 99.1 | 101.0 |
| | 8 weeks | 95.1 | 101.6 | 93.0 | 104.8 |
| 50° C./30% RH | 0 weeks | 94.2 | 103.8 | 98.3 | 103.5 |
| | 2 weeks | 92.6 | 98.5 | 94.0 | 101.7 |
| | 4 weeks | 92.4 | 101.4 | 95.0 | 101.1 |
| | 8 weeks | 96.3 | 101.1 | 96.7 | 102.6 |
| 50° C./50% RH | 0 weeks | 94.2 | 103.8 | 98.3 | 103.5 |
| | 2 weeks | 93.0 | 99.4 | 96.2 | 101.9 |
| | 4 weeks | 116.7 | 102.4 | 98.0 | 101.2 |
| | 8 weeks | 96.0 | 99.4 | 97.9 | 104.0 |
| 60° C./10% RH | 0 weeks | 94.2 | 103.8 | 98.3 | 103.5 |
| | 2 weeks | 92.7 | 101.2 | 97.6 | 103.7 |
| | 4 weeks | 91.9 | 99.8 | 99.0 | 103.5 |
| | 8 weeks | 93.5 | 101.9 | 99.4 | 103.7 |
| 60° C./40% RH | 0 weeks | 94.2 | 103.8 | 98.3 | 103.5 |
| | 2 weeks | 111.8 | 100.5 | 92.6 | 102.4 |
| | 4 weeks | 99.1 | 101.1 | 96.2 | 104.0 |
| | 8 weeks | 93.4 | 105.3 | 98.3 | 103.9 |

Figure 27:
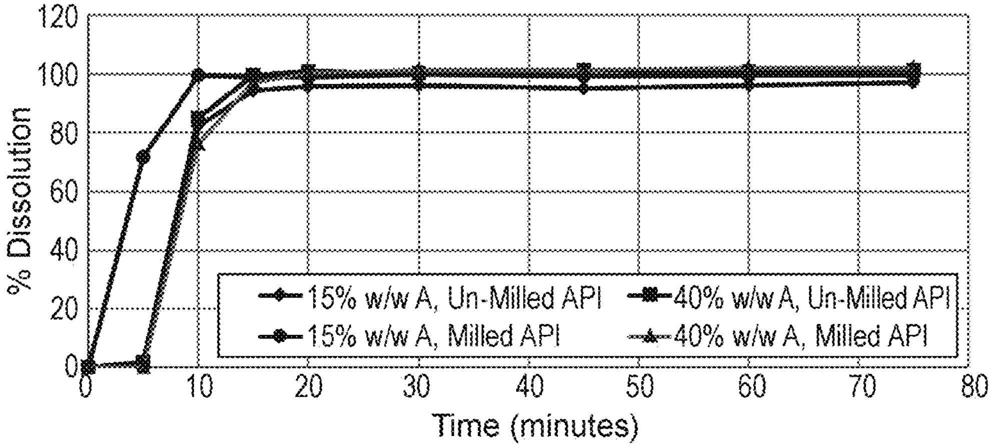
FIG. 27 provides dissolution data for experimental blends H, I, J, and K after twelve months at 30° C./65% RH. Blend H was unmilled 15% w/w API represented by the diamond-shaped points. Blend I was unmilled 40% w/w API represented by the square-shaped points. Blend J was milled 15% w/w API represented by the circle-shaped points. Blend K was milled 40% w/w API represented by the triangular-shaped points.
Figure 28A:
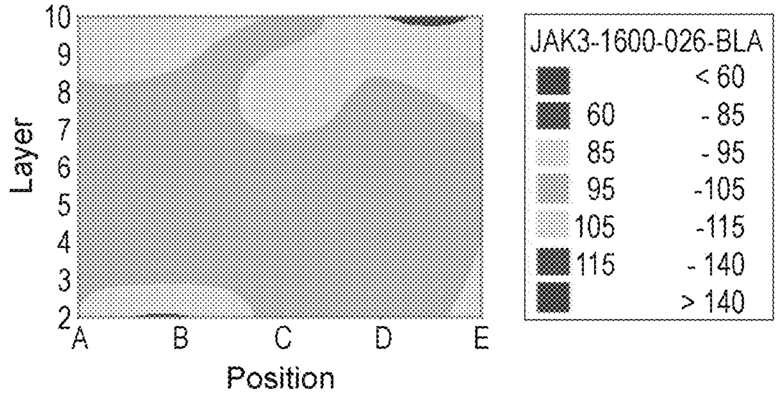
FIG. 28 provides segregation contour plots for PF-06651600-15 in experimental blends H, I, J, and K (respectively in panels (a), (b), (c) and (d)).
Figure 28B:
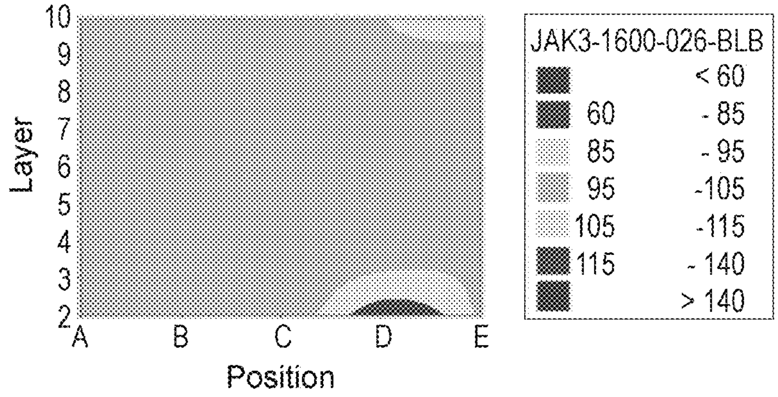
Figure 28C:
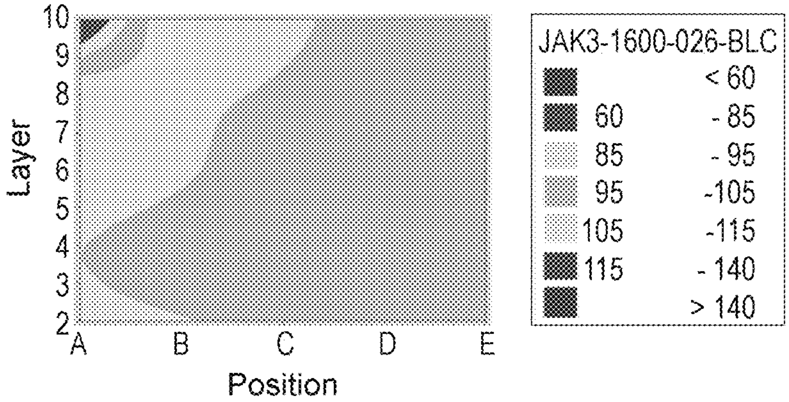
Figure 28D:
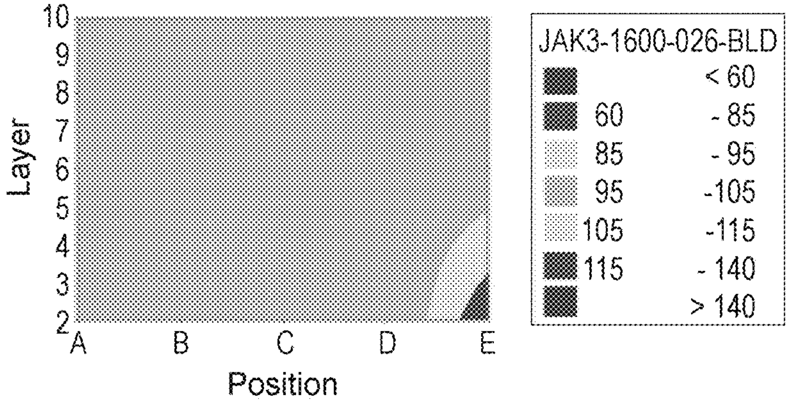

FIG. 27 provides a comparison of dissolution data for experimental blends H, I, J, and K after one year at 30°/65% relative humidity. All blends demonstrated greater than 80% dissolution after 30 minutes. The blend prepared with milled PF-06651600-15 at a concentration of 15% w/w Active was placed into gelatin capsules as opposed to the HPMC shells which were used to encapsulate the rest of the batches. This may explain the discrepancy recorded over the first 5 minutes of the dissolution test as there was a delay in the rupture of the HPMC capsules which in turn prevented the release of PF-06651600-15 resulting in the 0% dissolution recorded over the first five minutes of the dissolution test for blends H, I, and K.

FIG. 28 provides segregation contour plots for experimental blends H, I, J, and K. These plots provide a visual interpretation of PF-06651600-15 concentration throughout the blends. Results indicated that, despite hot spots within the blend, the 40% w/w active blends, I and K, were less prone to segregation regardless of PF-06651600-15 particle size. The 15% w/w active blends, H and J, demonstrated a greater variation in PF-06651600-15 concentration across the blend.

In summary, experimental formulations H, I, J, and K exhibited acceptable stability as shown by the appearance and amount of degradant produced by each blend. With regard to particle size, an increase in the particle size of PF-06651600-15 led to a reduction in dimer and total degradant product formation and also improved the blend manufacturing properties. With regard to product load, an increase in drug load reduced powder segregation. The data disclosed herein, therefore, supported commercial formulations comprised of microcrystalline cellulose, lactose monohydrate, polyvinylpyrrolidone (crospovidone), and glyceryl dibehenate with larger PF-06651600-15 particle size and higher percentage of PF-06651600-15 loads encapsulated in HPMC capsules.

In order to confirm the viability of the proposed commercial formulation, two batches of blend I (unmilled) and two batches of blend K (milled) were separately prepared and encapsulated in size 0 HPMC capsules (Table 23).

TABLE 23

Re-Prepared Blend I and Blend K Details

| Component | Blend I Un-Milled Batch 1 | Blend I Un-Milled Batch 2 | Blend K Milled Batch 1 | Blend K Milled Batch 2 |
|---|---|---|---|---|
| % PF-06651600-15 | 65.90* | 65.95* | 65.90* | 66.20* |
| % Microcrystalline Cellulose | 13.05 | 13.02 | 13.05 | 12.90 |
| % Lactose monohydrate | 13.05 | 13.03 | 13.05 | 12.90 |
| % Crospovidone | 3.00 | 3.00 | 3.00 | 3.00 |
| % Glyceryl Dibehenate | 5.00 | 5.00 | 5.00 | 5.00 |

*40% w/w API

The blends were then subjected to degradation studies to determine the percentage of dimer and total degradant products detected under the conditions and at the time points described in Table 24.

TABLE 24

Percentage Dimer and Total Product Degradants Detected for Re-Prepared Blends I and K

| Conditions | Time | Impurities | Blend I Un-Milled Batch 1 | Blend I Un-Milled Batch 2 | Blend K Milled Batch 1 | Blend K Milled Batch 2 |
|---|---|---|---|---|---|---|
| 30° C./ | 6 | % Dimer | 0.08 | 0.08 | 0.12 | 0.11 |
| 75% RH | months | % Total Deg. Products | 0.13 | 0.13 | 0.19 | 0.18 |
| 60° C./ | 28 | % Dimer | 0.06 | 0.05 | 0.08 | 0.06 |
| 40% RH | days | % Total Deg. Products | 0.06 | 0.05 | 0.08 | 0.06 |

The degradation results for blends I and K confirmed that both blends were stable and that blend I composed of the unmilled larger PF-06651600-15 particles was more stable than blend K composed of the milled smaller PF-06651600-15 particles. Therefore, based on the results described herein, an immediate release commercial formulation was postulated for 30 mg, 50 mg, and 100 mg doses of PF-06651600 in HPMC capsules comprising: about 60.10% PF-06651600-15 (37.50% active amount); about 15.95% microcrystalline cellulose; about 15.95% lactose monohydrate; about 3.00% crospovidone; and about 5.00% glyceryl dibehenate.

Immediate release capsules containing 30 mg, 50 mg, and 100 mg doses of PF-06651600-15 were prepared by combining: 60.10% PF-06651600-15; 15.95% microcrystalline cellulose (Avicel PH102); 15.95% lactose monohydrate (Fast Flo 316); 3.00% crospovidone type A (Polyplasdone XL); and 5.00% glyceryl dibehenate (Compritol 888 ATO, vegetable origin) in a suitably sized blending container and blended for 10 minutes at 30 rpm (300 revolutions) using a Turbula mixer. The blend was filtered through a cone mill fitted with a ~0.9 mm aperture (032R) screen at a speed of ~1000 rpm using a round rotor type and then blended for 10 minutes at 30 rpm (300 revolutions) using a Turbula mixer. 80.00 mgs of blend were filled into #4 Hypromellose capsules using a dosator disk encapsulation machine to provide the 30 mg doses of API (PF-06651600) in HPMC capsules. 133.333 mgs of blend were filled into #3 hypromellose capsules using a dosator disk encapsulation machine to provide the 50 mg doses of API (PF-06651600) in HPMC capsules. 266.667 mgs of blend were filled into #1 Hypromellose capsules using a dosator disk encapsulation machine to provide the 100 mg doses of API (PF-06651600) in HPMC capsules (Table 25).

TABLE 25

Immediate Release Commercial Formulations for 30 mg, 50 mg, and 100 mg Encapsulated Doses of API (PF-06651600)

| Components | 30 mg Dose | 50 mg Dose | 100 mg Dose |
|---|---|---|---|
| PF-06651600-15 (mgs) | 48.077 | 80.128 | 160.256 |
| Microcrystalline Cellulose (mgs) | 12.762 | 21.269 | 42.539 |
| Lactose Anhydrous (mgs) | 12.762 | 21.269 | 42.539 |
| Crospovidone A (mgs) | 2.400 | 4.000 | 8.000 |
| Glyceryl Dibehenate (mgs) | 4.000 | 6.667 | 13.333 |
| Total Fill Weight (mgs) | 80.00 | 133.333 | 266.667 |
| Hypromellose Capsule (number) | 4* | 3‡ | 1† |
| Total Weight (mgs) | 118.000 | 180.333 | 342.667 |

*Weight of #4 Hypromellose capsule was 38 mgs ± 3 mgs.
‡Weight of #3 Hypromellose capsule was 47 mgs ± 3 mgs.
†Weight of #1 Hypromellose capsule was 76 mgs ± 5 mgs.

We claim:

1. A stable immediate release formulation comprising about 15-67% 1-((2S,5R)-5-((7H-pyrrolo[2,3-d]pyrimidin-4-yl)amino)-2-methylpiperidin-1-yl)prop-2-en-1-one para-toluenesulfonate salt, about 12-40% microcrystalline cellulose, about 12-40% lactose monohydrate, about 2-4% crospovidone; and about 3-10% glyceryl dibehenate, wherein the formulation has 0.7% w/w or less of a dimer of 1-((2S,5R)-5-((7H-pyrrolo[2,3-d]pyrimidin-4-yl)amino)-2-methylpiperidin-1-yl)prop-2-en-1-one at 25-30° C./10-65% relative humidity for at least one year, wherein the stable immediate release formulation is free of, or comprises no more than 1.00% of magnesium stearate.

2. The stable immediate release formulation of claim 1, wherein the formulation has 0.2% w/w or less of a dimer of 1-((2S,5R)-5-((7H-pyrrolo[2,3-d]pyrimidin-4-yl)amino)-2-methylpiperidin-1-yl)prop-2-en-1-one para-toluenesulfonate salt at about 25° C./60% relative humidity for at least one year.

3. The stable immediate release formulation of claim 2, comprising 1-((2S,5R)-5-((7H-Pyrrolo[2,3-d]pyrimidin-4-yl)amino)-2-methylpiperidin-1-yl)prop-2-en-1-one para-toluenesulfonate salt with particle size 300.5 microns $D_{[v, 0.9]}$.

* * * * *